United States Patent [19]

Masaharu et al.

[11] Patent Number: 4,914,309

[45] Date of Patent: Apr. 3, 1990

[54] DISCRIMINATING TYPE FLAW DETECTOR FOR LIGHT-TRANSMITTING PLATE MATERIALS

[75] Inventors: Okafuji Masaharu; Takeoka Tatsuo; Ichinose Nagayoshi, all of Dosho; Abe Junichi, Ohaza-Kamifujisawa; Miyano Mitsuo, Ohaza-Kamifujisawa; Tanaka Kenji, Ohaza-Kamifujisawa, all of Japan

[73] Assignees: Nippon Sheet Glass Co., Ltd.; Kabushikikaisha Yaskawa Denki Seisakusho, both of Japan

[21] Appl. No.: 298,747

[22] PCT Filed: May 25, 1988

[86] PCT No.: PCT/JP88/00502

§ 371 Date: Mar. 20, 1989

§ 102(e) Date: Mar. 20, 1989

[87] PCT Pub. No.: WO88/09497

PCT Pub. Date: Dec. 1, 1988

[30] Foreign Application Priority Data

| May 27, 1987 | [JP] | Japan | 62-128089 |
| May 27, 1987 | [JP] | Japan | 62-128090 |
| May 28, 1987 | [JP] | Japan | 62-129639 |
| May 28, 1987 | [JP] | Japan | 62-129641 |
| May 28, 1987 | [JP] | Japan | 62-129644 |
| May 28, 1987 | [JP] | Japan | 62-79978 |
| May 29, 1987 | [JP] | Japan | 62-131524 |

[51] Int. Cl.$^4$ ............................................. G01N 21/47
[52] U.S. Cl. .................................... 250/572; 356/431; 356/446
[58] Field of Search ................ 250/571, 572; 356/429–431, 445–448

[56] References Cited

U.S. PATENT DOCUMENTS

| 3,806,256 | 4/1974 | Ishak ............................... 356/446 |
| 3,910,701 | 10/1975 | Henderson et al. ............. 356/446 |
| 3,999,864 | 12/1976 | Mutter ............................. 356/448 |
| 4,033,698 | 7/1977 | Demsky et al. ................. 356/446 |
| 4,218,144 | 8/1980 | Whitehouse et al. ........... 356/445 |
| 4,247,204 | 1/1981 | Merlen et al. .................. 356/431 |
| 4,311,393 | 1/1982 | Bartke ............................. 356/448 |
| 4,458,979 | 1/1984 | Röss ............................... 356/431 |
| 4,570,074 | 2/1986 | Jette ................................ 356/431 |
| 4,591,726 | 5/1986 | Schenk ........................... 356/431 |
| 4,666,309 | 5/1987 | Barry et al. ..................... 356/446 |

Primary Examiner—David C. Nelms
Assistant Examiner—Stephone B. Allen
Attorney, Agent, or Firm—McGlew & Tuttle

[57] ABSTRACT

This invention relates to a discriminating type flaw detector for detecting the types, sizes and locations of flaws existing in a light-transmitting plate material with high accuracy and high speed. A light-spot scanner (11) repeatedly scans a light-transmitting plate material with a light spot in the direction normal to the travelling direction of the light-transmitting plate material. When the light spot falls on a flaw in the light-transmitting plate material, the conditions of transmitted light, transmitted and diffused light, reflected light and reflected and diffused light change. These changes are detected by light receptors (12), converted into electrical signals in photoelectric converters (13), and processed into flaw data in a flaw data generating circuit (14). A flaw data acquisition circuit (15) collects flaw data, prepares a flaw pattern by combining the flaw data into flaw data blocks by flaw, and reads the addresses of the flaw data blocks as location data. The flaw pattern is compared with the flaw discriminating pattern table in an information processing device (17) to identify the types and sizes of flaws, and the locations of flaws are also detected based on the location data. The discriminating type flaw detector of this type is installed in a manufacturing line of glass plate and other light-transmitting plate materials, and the detection results are used as criteria for judging quality for the control of the manufacturing line or product sorting.

9 Claims, 38 Drawing Sheets

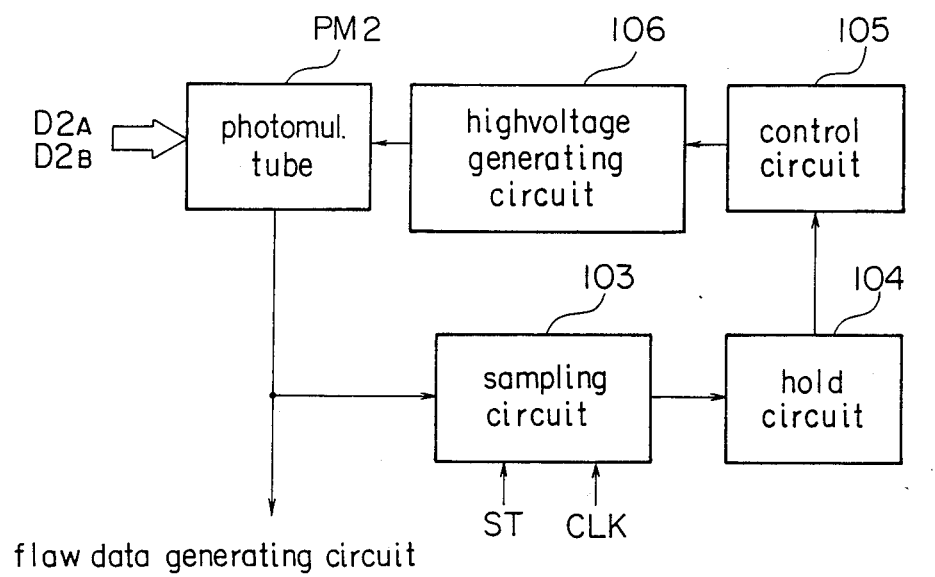
flow data generating circuit
FIG. 35
FIG. 36A
output signal
from PM2
FIG. 36B
ST
FIG. 36C
CLK
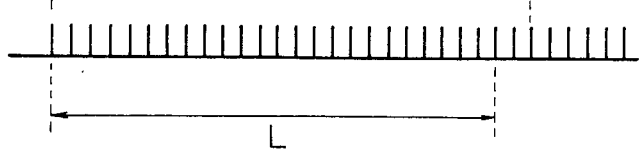

DISCRIMINATING TYPE FLAW DETECTOR FOR LIGHT-TRANSMITTING PLATE MATERIALS

TECHNICAL FIELD

This invention relates generally to a flying-spot type flaw detector that scans a glass plate, plastic plate or at least a plate material that transmits light (hereinafter referred to as a light-transmitting plate material) with a light spot to detect flaws present in a light-transmitting plate material, and more particularly to a discriminating type flaw detector for light-transmitting plate materials that can discriminate and detect the types, sizes and locations of detected flaws, and also relates to a flaw data acquisition circuit, light receptor, AGC (automatic gain control) device, and thickness correcting device. Furthermore, this invention also relates to a drip sensor using this discriminating type flaw detecting equipment.

BACKGROUND ART

A flaw detector for detecting flaws present in a light-transmitting material is needed to detect flaws in a transparent glass plate manufactured on a transparent glass plate manufacturing line, for example, and feed back the detection results to the transparent glass plate manufacturing process to prevent the occurrence of flaws at the location of generation so as to improve product yield.

The flaw detector of the conventional type for transparent glass plates includes one type as disclosed in Japanese Patent Application Laid-open No. 29988 of 1976, in which the presence of a flaw in a glass plate is known by detecting only the reflected light of a projected light beam with a light receptor, and another type as disclosed in Japanese Patent Application Laid-open No. 1184 of 1976, in which the presence of a flaw in a glass plate is known by detecting only the transmitted light of a projected light beam with a light receptor.

The flaw detector disclosed in the aforementioned Japanese Patent Application Laid-open No. 29988 of 1976 can detect a flaw on the surface of a glass plate, but cannot detect a flaw inside the glass plate.

The flaw detector disclosed in Japanese Patent Application Laid-open No. 1184 of 1976, on the other hand, can detect a flaw inside a glass plate, but it is impossible or extremely difficult to detect a flaw on the surface of the glass plate.

The aforementioned flaw detectors cannot detect and identify the types of flaws, such as bubbles formed by air bubbles remaining inside the glass plate, foreign matter remaining inside the glass plate, knots formed by almost molten foreign matter remaining inside the glass plate in a shape having a streaming tail, or drips formed by the metallic tin content of tin bath deposited on the glass plate surface. Moreover, detection of an air bubble, foreign matter, etc. on the same detection level with a single light receptor could result in overly detection of the foreign matter and insufficient detection of the air bubble.

In addition, the use of the conventional flaw detector which cannot detect the size of a flaw accurately makes it impossible to adopt the so-called two-blade glass plate sorting system in which the quality of transparent glass plates cut in the manufacturing process is sorted into high and low grades.

DISCLOSURE OF INVENTION

It is an object of this invention to provide a discriminating type flaw detector capable of detecting flaws in a light-transmitting plate material with high precision and high speed.

It is another object of this invention to provide a flaw data acquisition circuit, AGC circuit, thickness correcting device, and light receptor suitable for the discriminating type flaw detector.

It is still another object of this invention to provide a flaw detector capable of discriminating and detecting a drip in such a manner as to distinguish from other types of flaws.

Flaws in a glass plate include bubbles, foreign matter, knots, drips, etc., as noted earlier. When such a flaw exists in a glass plate, projecting a light spot on the flaw produces varied states of light, such as transmission, transmission and diffusion, reflection, and reflection and diffusion, depending on the type of the flaw. Eying this fact, the present applicant collected a large quantity of data through various experiments to see how the state of transmission, transmission and diffusion, reflection, or reflection and diffusion would change according to the types of flaws in a glass plate. Part of the analysis results of the data will be described in the following.

As shown in FIG. 1, when a light beam 3 is projected on a flaw 2 existing in a transparent glass plate 1 at a predetermined incident angle $\alpha$ with respect to the normal, a knot, foreign matter, or an air bubble produces a transmitted and diffused light beam. Particularly, a knot will produce the most paraxial transmitted and diffused light 5 that is closest to the optical axis of the transmitted light 4, a foreign material would produce paraxial transmitted and diffused light 6 which is close to the optical axis of the transmitted light 4, and a bubble would produce the least paraxial transmitted and diffused light 7, which is away from the optical axis of the transmitted light 4. All the bubble, foreign material, knot and drip reduce the quantity of transmitted light 4, while the drip increases the quantity of reflected light 8.

Consequently, if different light receptors each of which can detect transmitted light, the most paraxial transmitted and diffused light, paraxial transmitted and diffused light, the least paraxial transmitted and diffused light, and reflected light are provided to detect changes in the quantities of transmitted light and reflected light, and the presence/absence of the most paraxial transmitted and diffused light, paraxial transmitted and diffused light, and the least paraxial transmitted and diffused light, the types of flaws can be discriminated.

The above discussion is summarized in Table 1. In the table, a mark O denotes the ability of discriminating the type of a flaw.

TABLE 1

| Light Flaw | Transmitted light | Most paraxial transmitted/ diffused light | Paraxial transmitted/ diffused light | Least paraxial transmitted/ diffused light | Reflected light |
| --- | --- | --- | --- | --- | --- |
| Bubble | O | | | O | |
| Foreign matter | O | | O | | |
| Knot | O | O | | | |
| Drip | O | | | | O |

The present applicant found that the quantity of light detected by each light receptor is proportional to the size of a flaw. Consequently, the size of a flaw can be determined by detecting the quantity of light detected by each light receptor.

Although what has been described above is part of the knowledge obtained by the present applicant, it is also known that there is a certain relationship between the type of a flaw and the state of reflected and diffused light.

Based on the above consideration, the discriminating type flaw detector of this invention has a plurality of light receptors each of which detects at least more than two types of light beams among transmitted light, the most paraxial transmitted and diffused light, paraxial transmitted and diffused light, the least paraxial transmitted and diffused light, reflected light, and reflected and diffused light to convert the light beams received from the light receptors to electrical signals, produce flaw data containing the information representing the types and sizes of flaws by processing the electrical signals obtained, prepare a flaw pattern consisting of bit patterns corresponding to the flaws on a light-transmitting plate material by further processing the flaw data, and compare the flaw pattern thus obtained with a prestored flaw discriminating pattern table to judge the types and sizes of flaws.

The discriminating type flaw detector of this invention is also designed to detect the location of a flaw in a glass plate. Thus, the discriminating type flaw detector of this invention eventually can discriminate and detect the types, sizes and locations of flaws.

It is apparent that this invention can be applied to the detection of flaws not only in a glass plate but also in a plastic sheet and other plate materials that transmit light.

The discriminating type flaw detector for light-transmitting plate materials of this invention comprises a light-spot scanner that scans the entire surface of a travelling light-transmitting plate material with a light spot, a plurality of light receptors that receive more than two types of light beams among transmitted light, transmitted and diffused light, reflected light and reflected and diffused light from the light-transmitting plate material scanned by the light spot, a plurality of photoelectric converters that convert the light beams received by the light receptors to electrical signals, a flaw data generating circuit for producing flaw data containing the information on the types and sizes of flaws existing in the light-transmitting plate material by processing the electrical signals from the photoelectric converter, a flaw data acquisition circuit that collects the flaw data from the flaw data generating circuit, combines and processes the collected flaw data and produces a flaw pattern representing the types and sizes of flaws and the flaw location data, and an information processing device that discriminates at least the types and sizes of flaws by comparing the flaw pattern from the flaw data acquisition circuit with a prestored flaw discriminating pattern table, and discriminates the locations of flaws based on the flaw location data.

A suitable light receptor for use in such a discriminating type flaw detector is such that multiple optical fibers are used with the ends thereof arranged in a row to form a light-receiving surface. This type of light receptor, however, tends to cause variations in the waveform of the received light due to variations in the sensitivity of optical fibers, the fixing angle of the ends of optical fibers on the light-receiving side, and the degree of polishing of the light-receiving end face of optical fibers. To prevent this, a light diffuser is provided in front of the light-receiving surface. In the discriminating type flaw detector using a light receptor equipped with a light diffuser, detection of laws with high precision is possible because of freedom from variations in sensitivity.

The flaw data acquisition circuit has a first counter that counts a first pulse train relating to the location of a light-transmitting plate material in the direction normal to the travelling direction of the light-transmitting plate material and outputs a count value at the time of flaw data acquisition, a second counter that counts a second pulse train relating to the location of the light-transmitting plate material in the travelling direction and outputs the count value at the time of flaw data acquisition, an OR unit that accumulates flaw data for a plurality of scans for OR processing and outputs the processed flaw data at the timing of generation of the second pulse train, and a buffer memory that temporarily stores the outputs of the first and second counters and the OR unit.

In this flaw data acquisition circuit, a plurality of flaw data may be sometimes output for a single flaw from the OR unit, and as a result, the information processing device may have to process a plurality of flaw data for a single flaw. This may result in an increased burden on the software ofthe information processing device. Moreover, the flaw data output by the flaw data generation circuit based on changes in the quantity of light detected by each light receptor are not necessarily be output at the same timing at which a single flaw is scanned by the light spot. In such a case, the flaw data generated at a shifted timing have to be identified as those for that single flaw.

This problem can be overcome by providing a continuity judgement circuit which compresses the flaw data from the OR unit and judges the continuity of the compressed flaw data in the travelling direction and the direction normal to the travelling direction of a light-transmitting plate material.

The discriminating type flaw detector of this invention is adapted so that a light beam falls on a light transmitting plate material obliquely to prevent light beams from interfering with each other. With such a construction, if the thickness of the light-transmitting plate material changes, the optical axes of the transmitted light and the reflected light could be shifted, resulting in deteriorated light receiving sensitivity of each light receptor not only for the transmitted light and the reflected light but also for the diffused light. A thickness correcting device is provided to prevent deterioration of the detection sensitivity of the discriminating type flaw detector. In the discriminating type flaw detector of this invention, light transmittance could change in accordance with the thickness and color of a light-transmitting plate material, or the output of the light beam source could change, or the sensitivity of the photoelectric converter could deteriorate. In order to maintain the flaw detection sensitivity in such a case, it is necessary to keep the detection sensitivity constant. To this end, an AGC (automatic gain control) device is provided to automatically control the sensitivity, that is, gain of the photoelectric converter.

BRIEF DESCRIPTION OF DESCRIPTION

FIG. 35 is a diagram illustrating the electrical circuit portion of the first example of the AGC device.

FIGS. 36A, 36B and 36C are waveform diagrams of assistance in explaining the operation of the first example of the AGC device.

BEST MODE FOR CARRYING OUT THE INVENTION

Figure 1:
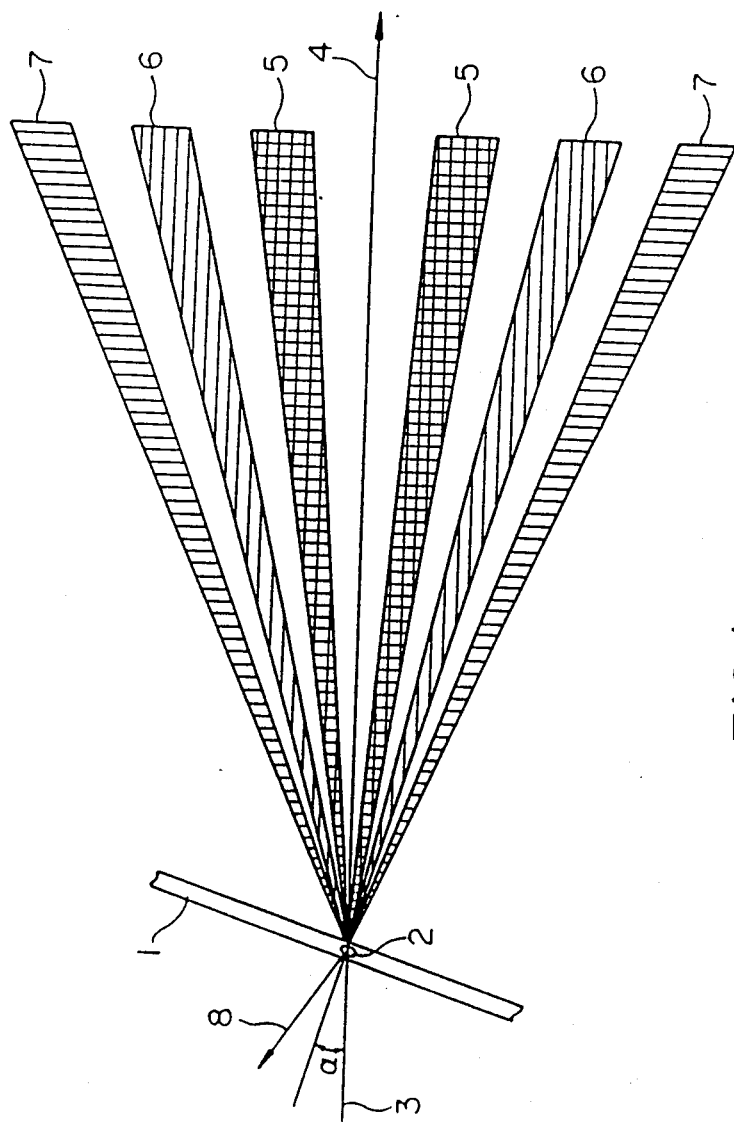
FIG. 1 is a diagram illustrating the conditions of the reflected light, transmitted light and transmitted and diffused light of a light beam falling upon a transparent glass plate having flaws.
Figure 2:
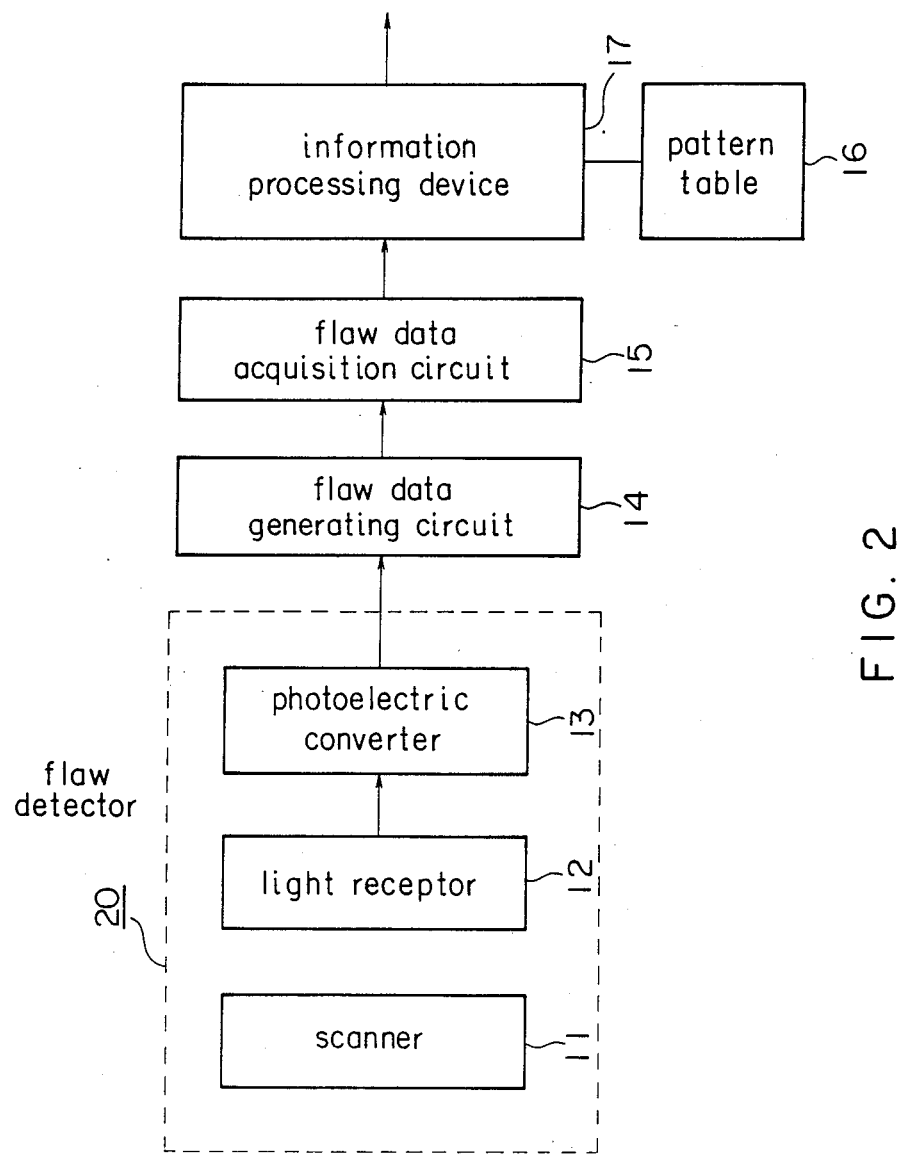
FIG. 2 is a block diagram illustrating the basic construction of a discriminating type flaw detector embodying this invention.

FIG. 2 is a block diagram outlining the overall construction of a discriminating type flaw detector for transparent glass plates. The discriminating type flaw detector comprises a scanner 11 which scans a travelling transparent glass plate with a laser spot formed by reflecting a laser beam with a rotating multiplanar mirror; a plurality of light receptors 12 for receiving the transmitted light, transmitted and diffused light and reflected light of the laser spot as the laser spot scans flaws in the travelling transparent glass plate; a photoelectric converter 13 which converts the light received by each light receptor to an electrical signal; a flaw data generating circuit 14 which generates flaw data containing information on the types and sizes of flaws by processing the electrical signal from the photoelectric converter 13; a flaw data acquisition circuit 15 which collects the flaw data generated by the flaw data generating circuit, a signal processing clock and a line synchronization signal, forms from the flaw data a flaw pattern consisting of bit trains representing the types and sizes of flaws existing in a glass plate, and adds information on the locations of flaws to the flaw pattern; and an information processing device 17 which receives the flaw pattern from the flaw data acquisition circuit 15 and the information on the locations of flaws, discriminates the types and sizes of flaws by comparing the flaw pattern with a prestored flaw discriminating pattern table 16, and feeds the discrimination results and the information on the locations of flaws to a host information processing system.

In the following, description will be made on a flaw detector 20 comprising a scanner 11, a light receptor 12 and a photoelectric converter.

Figure 3:
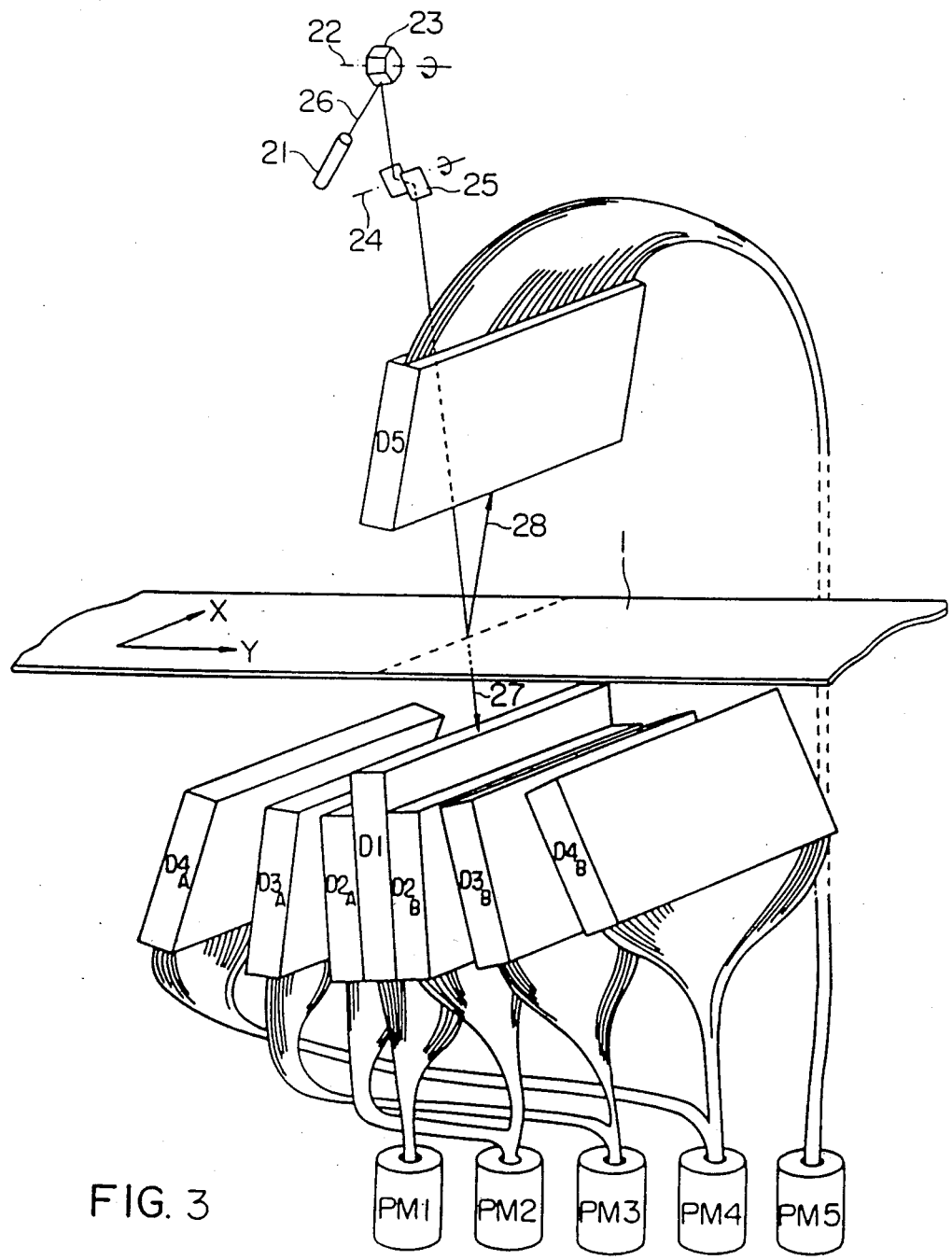
FIG. 3 is a perspective view of the flaw detector of the same.

FIG. 3 is a perspective view of a flaw detector 20, with the light receptor shown in an exaggerated form for clarity.

Figure 4:
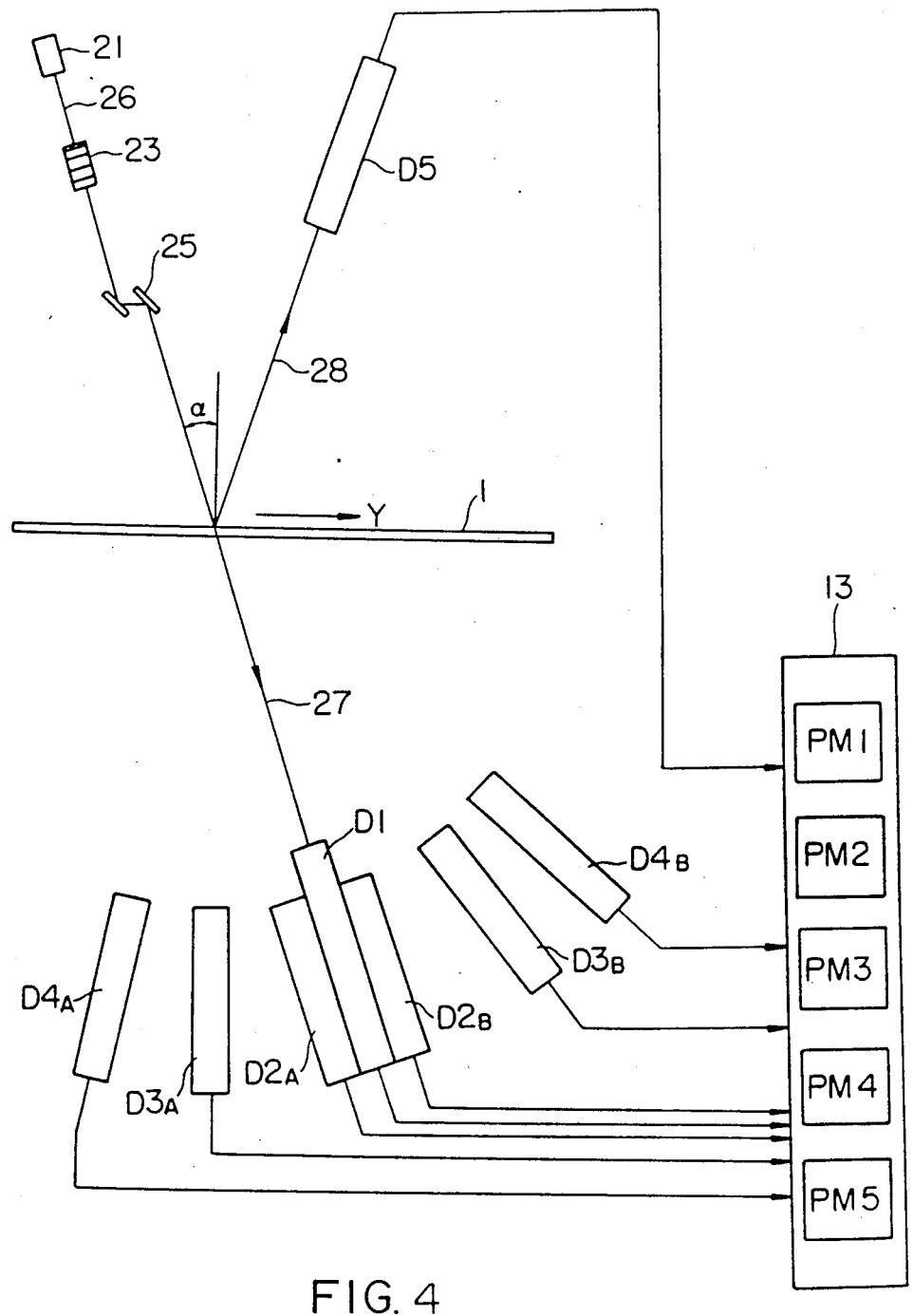
FIG. 4 is a side elevation of the flaw detector of the same.

FIG. 4 is an outline drawing of the flaw detector viewed in the direction normal to the travelling direction of a transparent glass plate. Like parts are indicated by like numerals in FIGS. 3 and 4.

The scanner 11 has a laser light source 21 emitting laser light, a rotating multiplanar mirror 23 rotating at high speed around an axis 22 parallel with the travelling direction of a transparent glass plate 1 (hereinafter referred to as the Y-axis direction), upon which a laser beam 26 from the laser light source 21 falls, and a parallel mirror assembly 25 for thickness correction which can change the angular location thereof by rotating around an axis 24 parallel with the across-the-width direction of the glass plate 1 (hereinafter referred to as the X-axis direction), that is, in the direction normal to the Y-axis direction. The location of the laser light source 21 is shown in FIG. 4 in a different way from the actual location thereof for clarity.

The scanner having the aforementioned construction is installed above the travelling transparent glass plate 1.

The laser beam 26 emitted from the laser light source 21 falls on the rotating multiplanar mirror 23 that rotates at high speed. The laser beam 26 is diverted by the rotating multiplanar mirror 23 towards the X-axis direction, reflected by the parallel-mirror assembly 25 and then falls on the travelling transparent glass plate 1 to scan the glass plate in the X-axis direction. Every time the reflecting surface of the rotating multiplanar mirror 23 is changed as the mirror 23 rotates, the laser beam 26 repeatedly scans the transparent glass plate 1. Since the transparent glass plate 1 travels in the Y-axis direction, the entire surface of the glass plate is scanned by the laser beam.

As shown in FIG. 4, the laser beam 26 arrives at the transparent glass plate 1 at an incident angle $\alpha$ with respect to a normal to the glass plate surface. This is to prevent interference of the light reflected by the rear surface of the transparent glass plate 1, then reflected again by the front surface and leaving the rear surface with the transmitted light 27. The value of $\alpha$ should preferably be more than 13°.

Next, the arrangement and construction of the light receptor will be described. On the opposite side to the side on which the scanner is installed, or below the transparent glass plate 1, provided are a light receptor D1 for detecting the transmitted light 27 two light receptors $D2_A$ and $D2_B$ for detecting the most paraxial transmitted and diffused light, two light receptors $D3_A$ and $D3_B$ for detecting the paraxial transmitted and diffused light, and two light receptors $D4_A$ and $D4_B$ for detecting the least paraxial transmitted and diffused light. Above the transparent glass plate 1, provided is a light receptor D5 for detecting the reflected light 28.

These multiple light receptors have essentially the same construction, each equipped with a slender linear light-receiving surface extending in the X-axis direction. In the following, the construction of a light receptor D1 will be described as a typical example.

Figure 5:
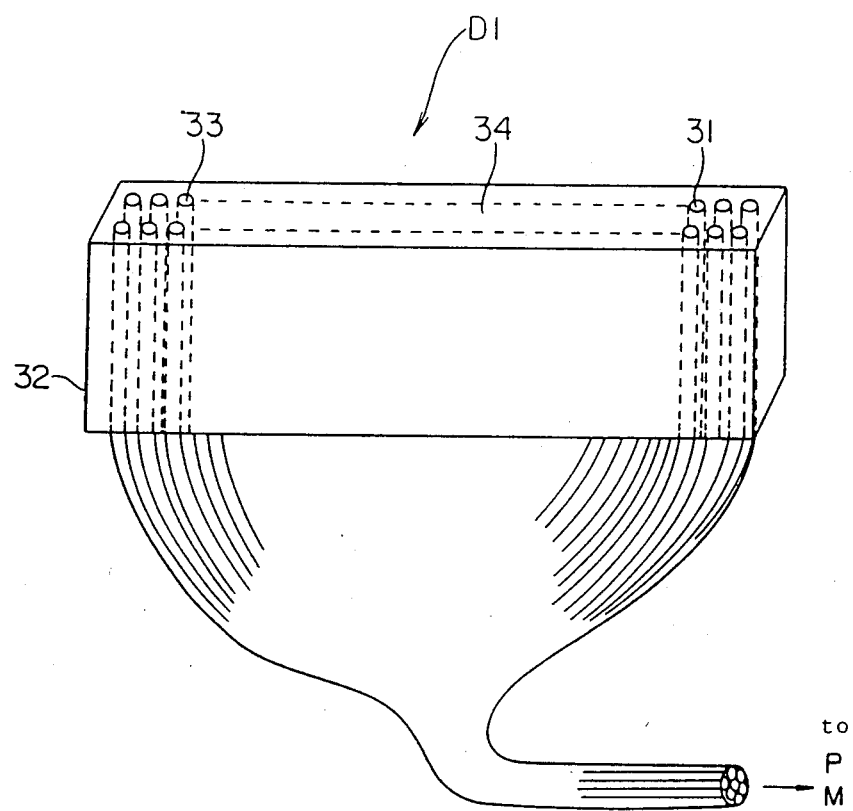
FIG. 5 is a perspective view of a light receptor.

FIG. 5 is a perspective view of the light receptor D1. The light receptor D1 consists of multiple optical fibers 31 which are arranged at one end thereof in two rows and held in place by casting filler resin to form the light receptor proper 32. The end faces 33 of the arranged multiple optical fibers 31 are assembled into a slender linear light-receiving surface 34. The other ends of the optical fibers 31 are bundled and connected to photomultiplier tubes, which will be described later.

Although the optical fibers are arranged in two rows in the above example, the mode of optical fiber arrangement is not limited to this arrangement.

When installing the light receptors D1, $D2_A$, $D2_B$, $D3_A$, $D3_B$, $D4_A$ and $D4_B$ of the abovementioned construction for detecting transmitted light and transmitted and diffused light, each light receptor is installed in such a manner that the light-receiving surface thereof is located with the effective light-receiving angles thereof. A typical relationship between the light receptor and the effective light-receiving angle thereof is shown in Table 2.

TABLE 2

| Light receptor | Effective light-receiving angle |
|---|---|
| D1 | 0°–±0.43° |
| $D2_A$, $D2_B$ | ±0.43°–±0.71° |
| $D3_A$, $D3_B$ | ±1.59°–±2.05° |
| $D4_A$, $D4_B$ | ±8.13°–±9.46° |

Figure 6:
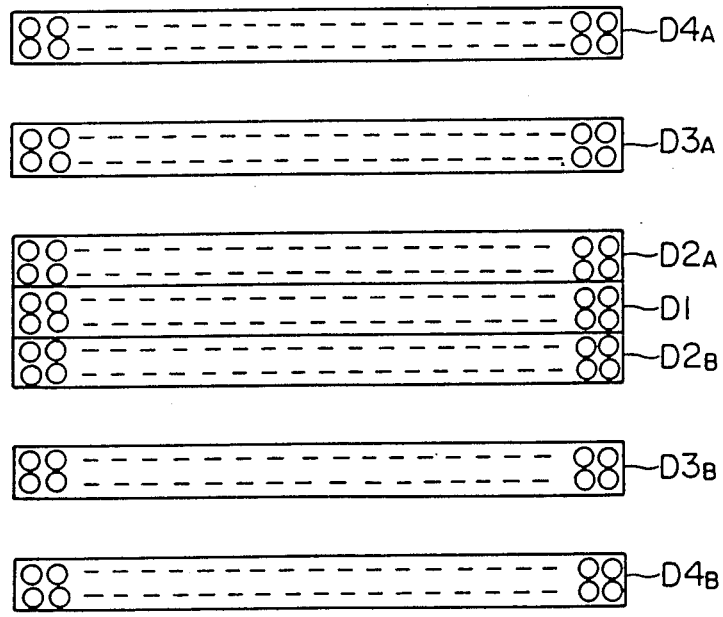
FIG. 6 is a plan view of the light-receiving surfaces of a plurality of light receptors for transmitted light and transmitted and diffused light.

FIG. 6 shows the light receptors D1, $D2_A$, $D2_B$, $D3_A$, $D3_B$, $D4_A$ and $D4_B$ arranged in such a fashion that the light-receiving surfaces thereof are located within the effective light-receiving angle shown in the table above, viewed from the light-receiving surfaces. The longitudinal direction of the light-receiving surface of each light receptor is parallel to the X-axis direction. Two light receptors each for detecting the most paraxial transmitted and diffused light, the paraxial transmitted and diffused light, and the least paraxial transmitted and diffused light are used in order to prevent these transmitted and diffused light beams from being overlooked.

As shown in FIGS. 3 and 4, the location of the light-receiving surface of the light receptor D1 for the transmitted light is shifted with respect to the optical axis from the location of the light-receiving face of the adjoining light receptors $D2_A$ and $D2_B$ for the most paraxial transmitted and diffused light to prevent the transmitted light from being further diffused by the light-receiving surface of the light receptor D1 and entering the light receptors $D2_A$ and $D2_B$.

The light receptor D5 for detecting the reflected light may be formed by optical fibers, as described above, but a diffuser box may be used to collect the light, which is then fed to a photomultiplier tube which will be described later, via optical fibers. In this case, it is recommended that a mask having a slit should be provided on the light-receiving face of the diffuser box to shield unwanted light.

The flaw detector 20 (FIG. 2) has five photomultiplier tubes PM1, PM2, PM3, PM4 and PM5 as photoelectric converters, as shown in FIG. 3, with the photomultiplier tube PM1 being connected to the other ends of the optical fibers of the light receptor D1, the photomultiplier tube PM2 being connected to the other ends of the optical fibers of the light receptors $D2_A$ and $D2_B$, the photomultiplier tube PM3 being connected to the other ends of the optical fibers of the light receptors $D3_A$ and $D3_B$, the photomultiplier tube PM4 being connected to the other ends of the optical fibers of the light receptors $D4_A$ and $D4_B$, and the photomultiplier tube PM5 being connected to the other ends of the optical fibers of the light receptor D5. Each photomultiplier tube converts received light into electrical signals.

Though not shown, an optical fiber for forming a start pulse are provided between the rotating multiplanar mirror 23 and the parallel mirror 25 of the scanner, and a photoelectric converter for converting the light received by these optical fibers into an electrical signal and a pulse shaper for forming a start pulse ST are provided. The start pulse ST is used as a start-to-scan signal in the flaw data acquisition circuit, which will be described later.

When the thickness of the transparent glass plate 1 changes, the light paths of the transmitted light, the transmitted and diffused light and the reflected light could be changed, with the result that the light beams fail to fall upon the light-receiving surfaces of the light receptors. In such a case, the light paths of the transmitted light and the transmitted and diffused light, for example, can be kept unchanged by changing the light path of the incident light on the glass plate by turning the parallel-mirror assembly 25. When the parallel-mirror assembly 25 is adjusted to keep the light paths of the transmitted light and the transmitted and diffused light unchanged, the light path of the reflected light could be changed. This can be corrected by moving the light receptor D5 or the mask of the diffuser box if the light receptor D5 has such a diffuser box.

The method and apparatus for such thickness correction will be described later in greater detail.

Now, the operation of the flaw detector having the abovementioned construction will be described for the case where a laser beam scans a flaw existing in the transparent glass plate 1.

When the laser beam falls upon a flaw present in a transparent glass plate, the quantities of the transmitted light and the reflected light change in accordance with the type of flaw (foreign matter, bubble, knot, drip), and at the same time, the transmitted and diffused light is generated.

In the case of a knot, for example, when the incident laser beam falls upon the knot, the quantity of the transmitted light changes, and at the same time, the most paraxial transmitted and diffused light is generated. The change in the quantity of the transmitted light is detected by the light receptor D1, fed to the photomultiplier tube PM1 and converted into an electrical signal. The most paraxial transmitted and diffused light, on the other hand, falls on the light-receiving faces of the light receptors $D2_A$ and $D2_B$. The most paraxial received transmitted and diffused light is fed to the photomultiplier tube PM2 and converted to an electrical signal.

Similarly, if the flaw is a bubble, as the incident laser beam falls on the bubble, the quantity of the transmitted light changes, and at the same time, the least paraxial transmitted and diffused light is generated. The least paraxial transmitted and diffused light is received by the light receptors $D4_A$ and $D4_B$, fed to the photomultiplier tube PM4 and converted to an electrical signal.

Similarly, in the case of a drip, when the incident laser beam arrives at the drip, the quantity of the transmitted light changes, and at the same time the quantity of the reflected light also changes. The change in the reflected light is detected by the light receptor D5, fed to the photomultiplier tube PM5 and converted to an electrical signal.

In this way, the changes in the quantities of the transmitted light and the reflected light caused by the flaw in the transparent glass plate, and the most paraxial transmitted and diffused light, the paraxial transmitted and diffused light and the least paraxial transmitted and diffused light are sent from the flaw detector 20 to the flaw data generating circuit 14 (FIG. 2) in the form of electrical signals.

Next, the construction of the flaw data generating circuit 14 which generates flaw data containing information on the types and sizes of flaws by processing the electrical signals fed from the photomultiplier tubes PM1, PM2, PM3, PM4 and PM5 of the flaw detector will be described in the following.

Figure 7:
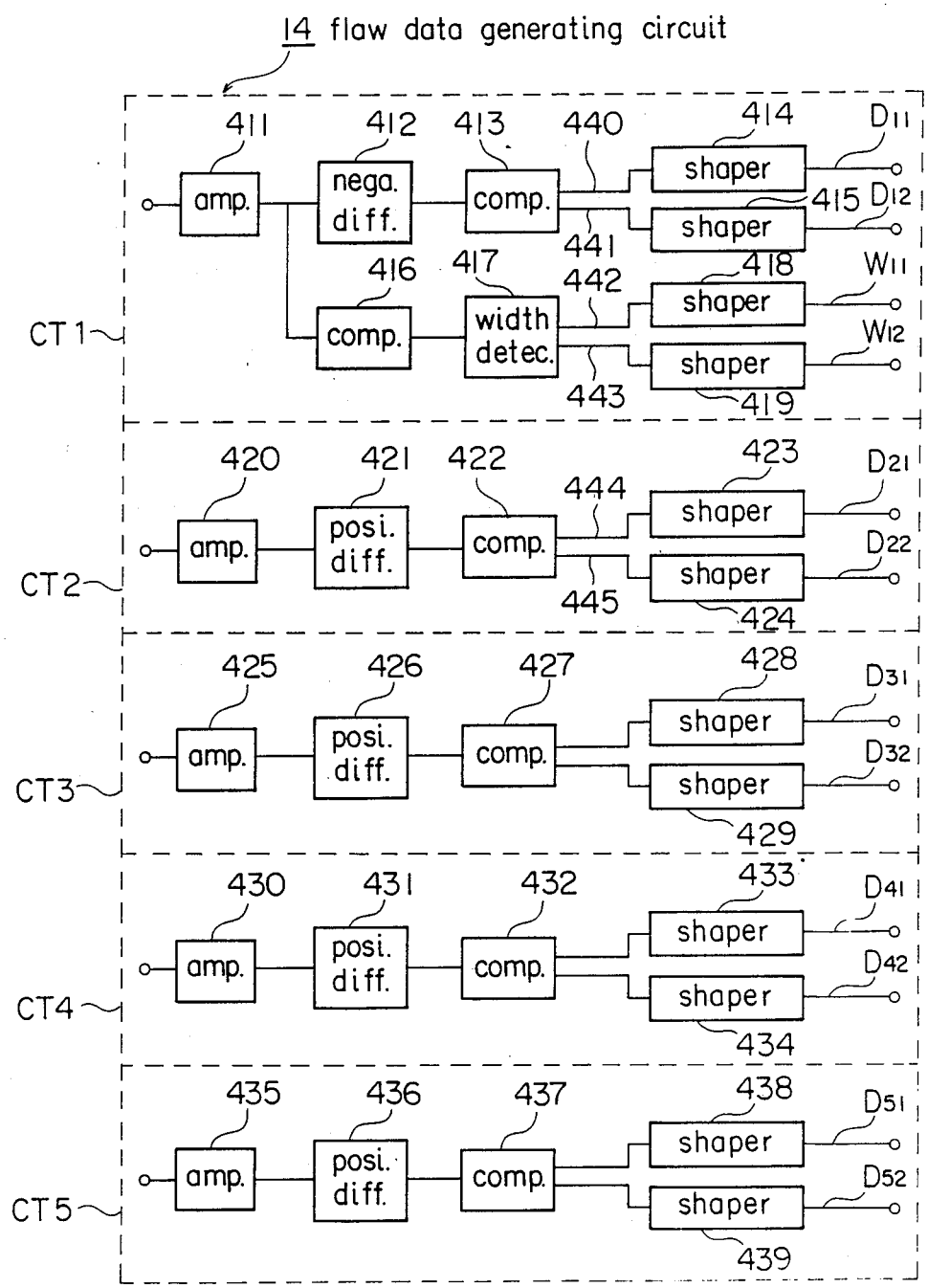
FIG. 7 is a block diagram of a flaw data generating circuit.
Figure 8A:
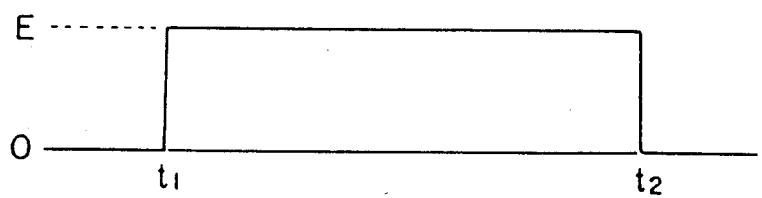
FIGS. 8-10 are waveform diagrams of assistance in explaining the operation of the flaw data generating circuit.
Figure 8B:
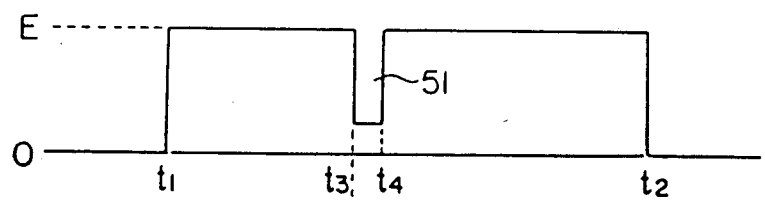
Figure 8C:
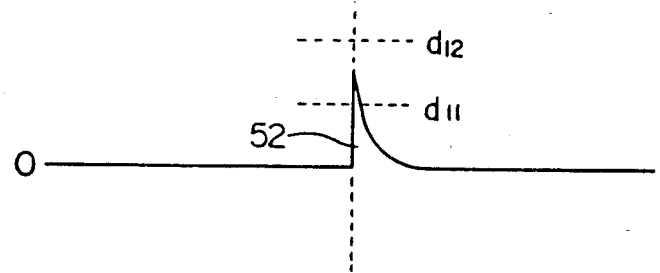
Figure 8D:
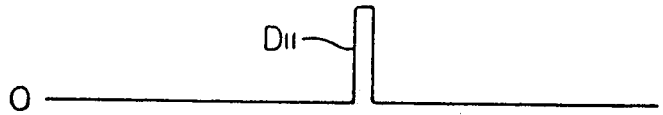

FIG. 7 shows an example of the flaw data generating circuit. The flaw data generating circuit comprises flaw data generating portions CT1, CT2, CT3, CT4 and CT5 for generating flaw data by processing the electrical signals from the photomultiplier tubes PM1, PM2, PM3, PM4 and PM5.

The flaw data generating portion CTi consists of an amplifier 411 for amplifying the electrical signal from the photomultiplier tube PM1, a negative differentiator 412 for differentiating the fall of the signal from the amplifier 411, a comparator 413 for comparing the level of the signal from the negative differentiator 412 with two detection levels, pulse shapers 414 and 415 for pulse-shaping the two signals output by the comparator 413, respectively, a comparator 416 for comparing the signal from the amplifier 411 with a detection level, a width detector 417 for comparing the width of the signal from the comparator 416 with two width judgement levels, and pulse shapers 418 and 419 for pulse-shaping the two signals output by the width detector 417.

The flaw data generating portion CT2 consists of an amplifier 420 for amplifying the electrical signal from the photomultiplier tube PM2, a positive differentiator 421 for differentiating the rise of the signal from the amplifier 420, a comparator 422 for comparing the level of the signal from the positive differentiator 421 with two detection levels, and pulse shapers 423 and 424 for pulse-shaping the two signals output by the comparator 422, respectively.

As the flaw data generating portions CT3, CT4 and CT5 have the same construction as the flaw data generating portion CT2, description has been omitted by giving only reference numerals to the elements thereof.

Next, the operation of the flaw data generating circuit 14 will be described, referring to FIGS. 8, 9 and 10.

To begin with, the operation of the flaw data generating portion CT1 will be described. The flaw data generating portion CT1 generates flaw data containing information on the types and sizes of laws from the electrical signal formed by the photomultiplier tube PM1 by converting the transmitted light detected by the light receptor D1.

The amplifier 411 amplifies the electrical signal sent from the photomultiplier tube PM1. FIG. 8 (a) shows the waveform of the output voltage of the amplifier 411 when the laser beam of the flaw detector performs one scan on a transparent glass plate having no flaws in the X-axis direction. The waveform indicates that the transmitted light is received by the light receptor D1 during one scan from time $t_1$ to time $t_2$, and the output level is E volts. In this way, the light receptor D1 receives transmitted light at all times during one scan.

When a flaw is present in a transparent glass plate, as a laser beam falls upon the flaw, the quantity of the transmitted light is reduced, generating a fall pulse 51 in the output waveform as shown in FIG. 8 (b). In the figure, the fall pulse is shown in an exaggerated form for convenience of explanation, and it is assumed that the pulse falls at time $t_3$ and rises at time $t_4$. The fall level of the fall pulse 51 is proportional to the size of the flaw; the larger the size of flaw the larger becomes the width (from time $t_3$ to time $t_4$) of the fall pulse.

The negative differentiator 412 negatively differentiates the output of the amplifier 411 and outputs a differentiated pulse 52 which rises at the fall time $t_3$ of the fall pulse 51. The magnitude of the differentiated pulse is proportional to the fall level of the fall pulse 51.

The differentiated pulse 52 from the negative differentiator 412 is input to the comparator 413. The comparator 413 has two detection levels $d_{11}$ and $d_{12}$ ($d_{11} < d_{12}$) with which the rise level of the input differentiated pulse 52 is compared If the rise level of the input differentiated pulse is higher than the detection level $d_{11}$, the comparator 413 outputs a pulse from the first output terminal 440 thereof, and if the input differentiated pulse is higher than the detection level $d_{12}$, the comparator 413 then outputs a pulse from the second output terminal 441 thereof. These pulses are shaped in the pulse shapers 414 and 415 and output as flaw data $D_{11}$ and $D_{12}$. In the case of the differentiated pulse 52 shown in FIG. 8 (c), as the rise level thereof is higher than the detection level $d_{11}$ and lower than the detection level $d_{12}$, flaw data $D_{11}$ shown in FIG. 8 (d) is output. The difference between the flaw data $D_{11}$ and $D_{12}$ as discussed above represents the size of a flaw.

The electrical signal from the amplifier 411 is input to the comparator 416 and then to the width detector 417 for width judgement processing. This width judgement processing is used for judgement in the so-called two-grade sorting process in which glass plates after cutting are sorted into high and low quality grades.

Figure 9A:
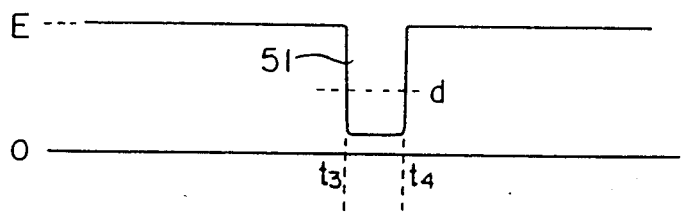
Figure 9B:
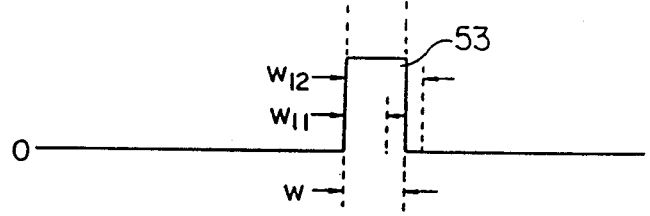
Figure 9C:
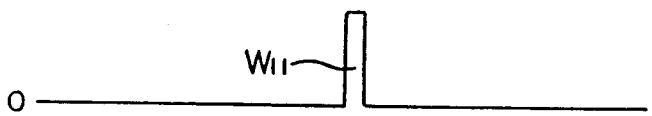

Now this width judgement processing will be described, referring to FIG. 9 showing waveforms. The waveform shown in FIG. 9 (a) is the portion of the fall pulse 51 in the waveform shown in FIG. 8 (b), which is shown by expanding the time axis. The comparator 416 has a detection level d, and therefore if the fall level of the fall pulse 51 exceeds the detection level d, the comparator 416 outputs a pulse 53 having a width equal to the width w (from time $t_3$ to time $t_4$) when the fall pulse 51 is sliced with the detection level d.

The width detector 417 has two width judgement levels $w_{11}$ and $w_{12}$ ($w_{11} < w_{12}$). and compares the width w of the Input pulse 53 with these judgement levels. The width detector 417 outputs a pulse from the first output terminal 442 thereof when the width w is larger than the judgement level $w_{11}$, and outputs a pulse from the second output terminal 443 when the width w is larger than the judgement level $w_{12}$. These pulses are shaped in the pulse shapers 418 and 419, and output as flaw data $W_{11}$ and $W_{12}$. In the case of the pulse 53 shown in FIG. 9 (b), the width w is larger than the judgement level $w_{11}$ and smaller than the judgement level $w_{12}$, so flaw data $W_{11}$ as shown in FIG. 9 (c) is output.

The difference between the flaw data $W_{11}$ and $W_{12}$ as discussed above represents the size of a flaw. These flaw data $W_{11}$ and $W_{12}$ are used as judgement data for sorting glass plates, particularly of lower grades in the two-grade sorting process.

Figure 10A:
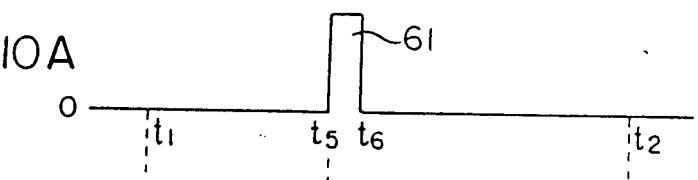
Figure 10B:
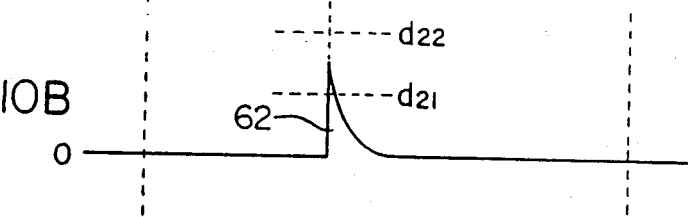
Figure 10C:

Next, the operation of the flaw data generating portion CT2 will be described, referring to FIG. 10 showing waveforms. The flaw data generating portion CT2 produces flaw data containing information on the types and sizes of flaws from the electrical signals produced by converting the most paraxial transmitted and diffused light detected by the light receptors $D2_A$ and $D2_B$ with the photomultiplier tube PM2. Electrical signals are fed from the photomultiplier tube PM2 only when a knot is scanned by the laser beam. FIG. 10 (a) shows the waveform of an electrical signal generated by the amplifier 420 when the knot is scanned. A rise pulse 61 is generated from time $t_5$ to time $t_6$. In the positive differentiator 421, the output of the amplifier 420 is positively differentiated, and a differentiated pulse 62 which rises at the rise time $t_5$ of the rise pulse 61 is output. The level of this differentiated pulse is proportional to the rise level of the rise pulse 61.

The differentiated pulse 62 from the positive differentiator 421 is input to the comparator 422. The comparator 422 has two detection levels $d_{21}$ and $d_{22}$ ($d_{21} < d_{22}$), as shown in the waveform shown in FIG. 10 (b), and compares the rise level of the input differentiated pulse 62 with these detection levels.

The comparator 422 outputs a pulse from the first output terminal 444 thereof if the rise level of the input differentiated pulse 62 is higher than the detection level $d_{21}$, and outputs a pulse from the second output terminal 445 if the rise level of the input differentiated pulse 62 is higher than the detection level $d_{22}$. These pulses are shaped in the pulse shapers 423 and 424, and output as flaw data $D_{21}$ and $D_{22}$. In the case of the differentiated pulse 62 shown in FIG. 10 (b), as the rise level thereof is higher than the detection level $d_{21}$ and lower than $d_{22}$, flaw data as shown in FIG. 10 (c) is output. The difference between the flaw data $D_{21}$ $D_{22}$ as discussed above represents the size of a flaw (knot).

With similar operations, flaw data $D_{31}$, $D_{32}$, $D_{41}$, $D_{42}$, $D_{51}$, and $D_{52}$ relating to foreign matter, a bubble, a drip are output from the flaw data generating portions CT3, CT4 and CT5.

As described above, flaw data $D_{11}$, $D_{12}$, --- $D_{52}$ containing information representing the types and sizes of flaws are output from the flaw data generating circuit 14, and sent to the flaw data acquisition circuit 15 (FIG. 2) In the following description, it is assumed that flaw data expressed by a pulse corresponds to a bit "1".

Next, the construction of the flaw data acquisition circuit will be described.

Figure 11:
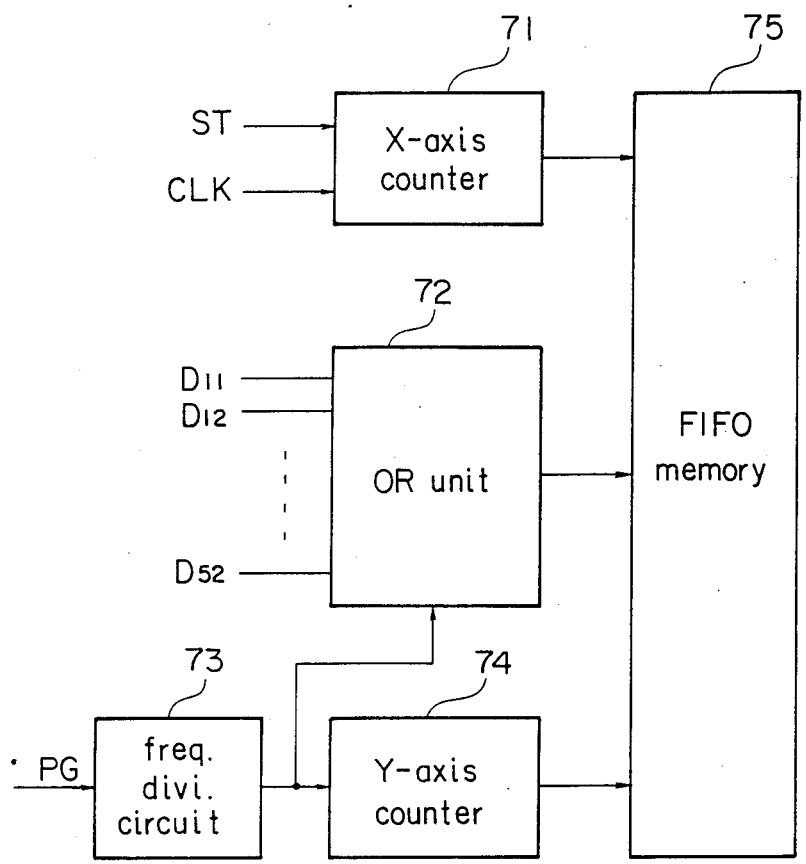
FIG. 11 is a block diagram illustrating an example of the flaw data acquisition circuit.

FIG. 11 shows a typical construction of the flaw data acquisition circuit, which comprises an X-axis counter 71 an OR unit 72, a frequency division circuit 73, a Y-axis counter 74 and a FIFO (first-in first-out) memory 75.

The X-axis counter 71 is a counter that counts clock signals for X-coordinate division, and is reset by a start pulse that is a start-to-scan signal. The start pulse ST is obtained in such a manner that the laser beam reflected by the rotating multiplanar mirror 23 of the flaw detector 20, as described above, is picked up at a given location via an optical fiber, converted photoelectrically to an electrical signal, and waveform-shaped. The X-axis counter 71 outputs a counter value at the time when the flaw data is collected as an X-coordinate location data.

The OR unit 72 is a unit which accumulates the flaw data for multiple scans from the flaw data generating circuit, and outputs the flaw data at a predetermined timing. Such an OR unit has been disclosed in Japanese Patent Publication No. 39415 of 1981, "Flaw Detection Equipment."

The frequency division circuit 73 divides the frequency of a line synchronization signal PG corresponding to the moving distance along the line of a glass plate, as supplied by the pulse generator (not shown), and enters the frequency-divided line synchronization signal PG to the OR unit 72. The OR unit 72 outputs the accumulated flaw data at the timing of the frequency-divided line synchronization signal PG.

The Y-axis counter 74 counts the line synchronization signal PG frequency-divided by the frequency division circuit 73, and outputs the count value as Y-coordinate location data. When the data transferred from the flaw data acquisition circuit is stored in the memory of the information processing device 17, the location of the Y-coordinate can be identified through software processing, without using hardware such as a Y-axis counter, by adding "0" to every set of data and counting the number of "0s". This method, however, cannot be considered suitable because the Y-coordinate location may be misidentified upon completion of one cycle of data storage in a limited capacity of the memory of the information processing device 17.

The FIFO memory 75 temporarily stores the X-coordinate location data from the X-coordinate counter 71, the flaw data from the OR unit 72 and the Y-coordinate location data from the Y-axis counter 74. Then the flaw data and the flaw location data are transferred from the FIFO memory 75 to the memory of the information processing device 17 by direct memory access (DMA).

The FIFO memory 75 is provided for the following reason. If the flaw data accumulated in the OR unit 72 is transferred directly to the memory of the information processing device 17 by direct memory access every time a flaw is detected, the flaw data could be missing because of the inability of collecting flaw data during DMA, resulting in failure of flaw detection. By temporarily storing the X-coordinate location data, the flaw data and the Y-coordinate location data in the FIFO memory 75, and transferring these data to the memory of the information processing device 17 by DMA between the FIFO memory 75 and the memory of the information processing device 17 in accordance with the data processing speed of the information processing device 17, all the flaw data can be positively collected.

Figure 12:
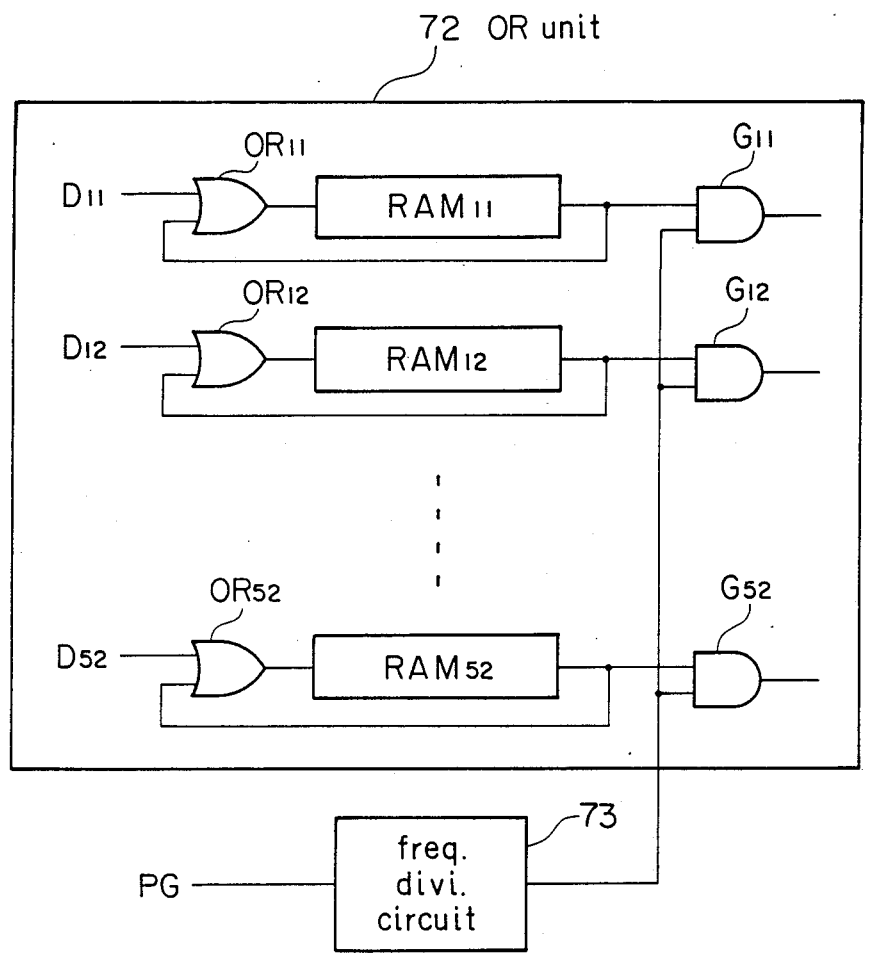
FIG. 12 is a circuit diagram of an OR unit.

FIG. 12 shows a typical example of the OR unit 72. The OR unit comprises logic OR circuits $OR_{11}$, $OR_{12}$, $-OR_{52}$ corresponding to flaw data $D_{11}$, $D_{12}$, $-D_{52}$ of multiple types, random access memories $RAM_{11}$, $RAM_{12}$, $-RAM_{52}$, and gate circuits $G_{11}$, $G_{12}$, $-G_{52}$.

Figure 13:
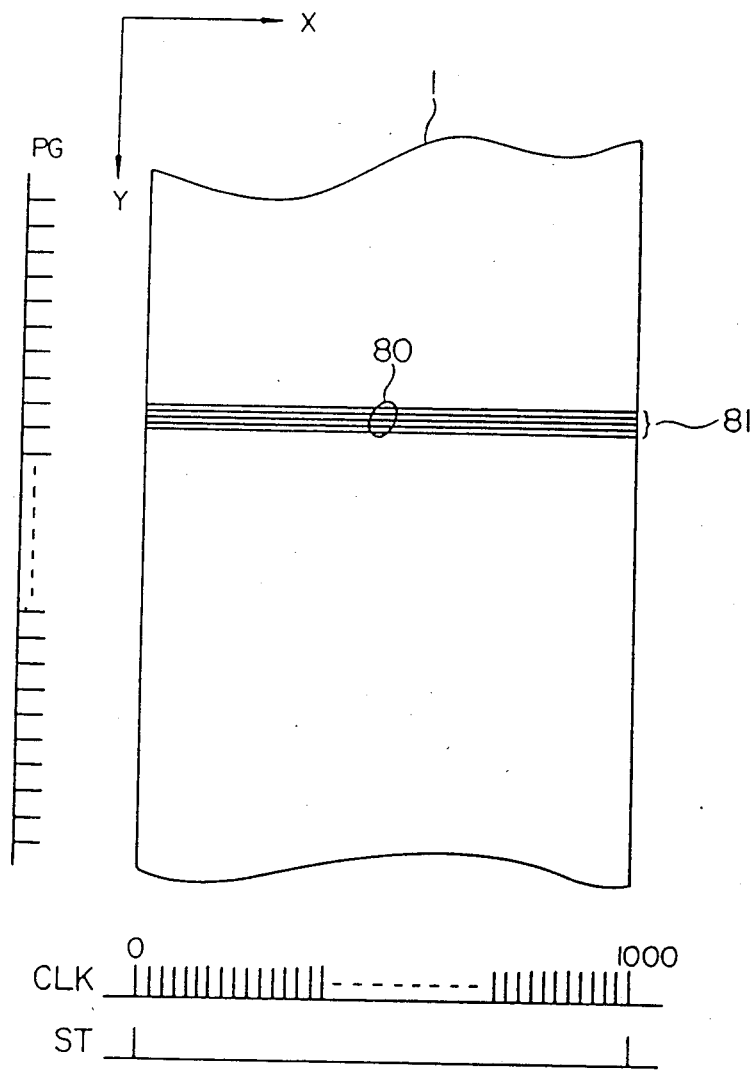
FIGS. 13 and 14 are diagrams of assistance in explaining the operation of the OR unit.
Figure 14:
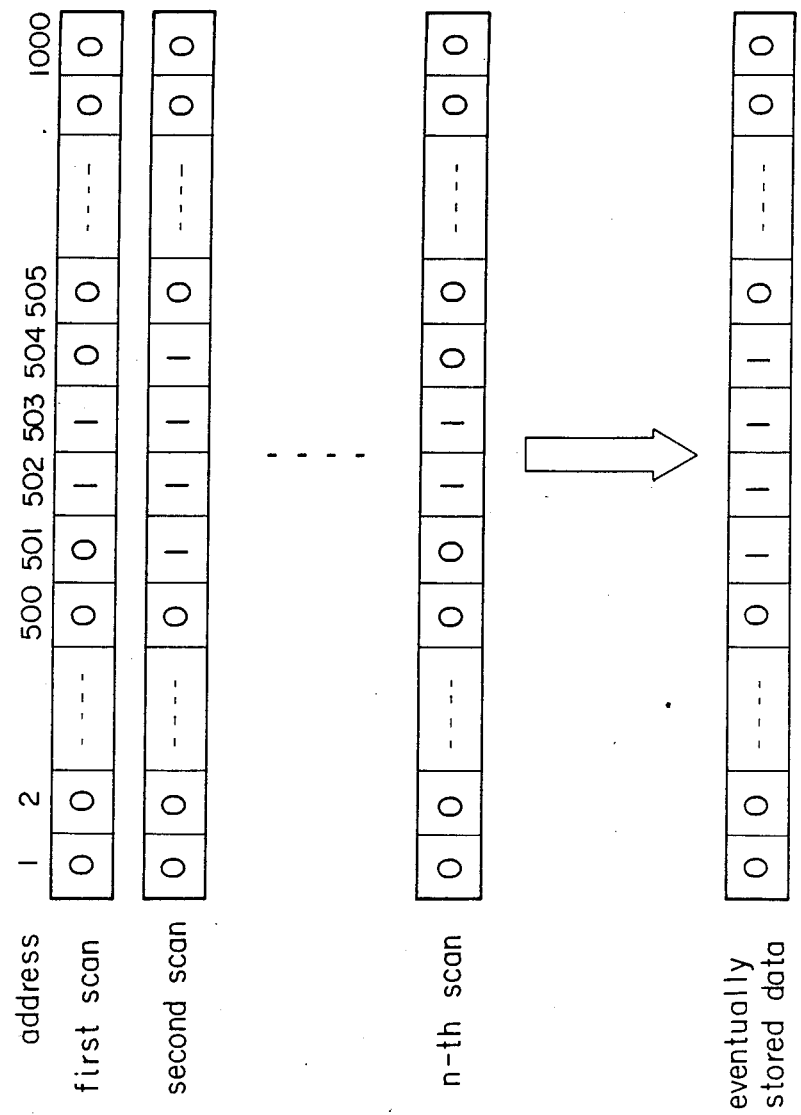

FIGS. 13 and 14 are diagrams of assistance in understanding the operation of the OR unit 72; FIG. 13 being a block diagram illustrating the relationship among scanning by a laser spot, a clock CLK and a frequency-divided line synchronization signal PG, and FIG. 14 being a digram illustrating the state of accumulating flaw data $D_{11}$ in the $RAM_{11}$ of the OR unit. In the following, accumulation of the flaw data $D_{11}$ as an example of the functions of the OR unit will be described, referring to these figures. It is now assumed that a glass plate is scanned n times in the X-axis direction by the laser beam spot during the line synchronization signal PG after frequency division. In FIG. 13, a scanning line by the laser beam spot is indicated by reference numeral 81. It is assumed that each RAM of the OR unit 72 has up to 1000 addresses. Each address in a RAM corresponds to the order of a clock CLK.

If there is a flaw 80 in a transparent glass plate 1, as shown in FIG. 13, a flaw data $D_{11}$ entered from the flaw data generating circuit at the first scan is written in the $RAM_{11}$, "1" bits are entered into the addresses 502 and 503. A flaw data $D_{11}$ entered at the second scan is ORed with the flaw data read from the $RAM_{11}$ in the logic OR circuit $OR_{11}$, and rewritten in the $RAM_{11}$, —and a flaw data $D_{11}$ entered at the n-th scan is ORed with the flaw data read from the $RAM_{11}$ in the logic OR circuit $OR_{11}$, and rewritten in the $RAM_{11}$. Thus, "1" bits are eventually stored in the addresses 501 to 504. In this way, the flaw data $D_{11}$ accumulated in the $RAM_{11}$ are output to the FIFO memory 75 via the gate circuit $G_{11}$ at the timing of the line synchronization signal PG frequency-divided in the frequency division circuit 73.

Since those flaws existing within a very close range in the Y-axis direction are judged as the same flaw through the abovementioned processing in the OR unit, the amount of information being processed in the information processing device can be reduced. As a result, the travelling speed of the glass plate can be increased, leading to increased inspection speed; or with the glass-plate travelling speed constant, detection sensitivity can be improved several times.

Now, the operation of the flaw data acquisition circuit will be described in greater detail, referring to FIG. 11 again. A start pulse ST and a clock CLK are input in the X-axis counter 71, flaw data $D_{11}$, $D_{12}$, $-D_{52}$ from the flaw data generating circuit 14 are input in the OR unit 72, and a line synchronization signal PG is input in the frequency division circuit 73. The X-axis counter 71 counts clocks CLK, and outputs in the FIFO memory 75 the count value of clocks CLK at the time of collection of a flaw data as an X-coordinate location data. The X-axis counter is then reset by a start pulse signal ST.

The OR unit 72 accumulates each flaw data $D_{11}$, $D_{12}$, $-D_{52}$ for multiple scans, and outputs them to the FIFO memory 75 at the timing of the line synchronization signal PG frequency-divided by the frequency division circuit 73, as described above with reference to FIGS. 13 and 14.

The Y-axis counter counts the line synchronization signal PG frequency-divided in the frequency division circuit 73, and outputs the count value to the FIFO memory 75 as a Y-coordinate location data at the time of flaw data entry. The Y-axis counter 74 is reset through software processing.

As described above, the X-coordinate location data, the flaw data and the Y-coordinate location data are temporarily stored in the FIFO memory 75, and then transferred to the memory of the information processing device 17 by DMA between the FIFO memory 75 and the memory of the information processing device 17. This data transfer is carried out in accordance with the data processing speed of the information processing device 17. Consequently, all the flaw data can be collected without fail.

In addition, since detection of the Y-coordinate location data is performed in terms of hardware, that is, with the Y-axis counter, not in terms of software, there is no problem of erroneous identification of the Y-coordinate location of a flaw.

Figure 15:
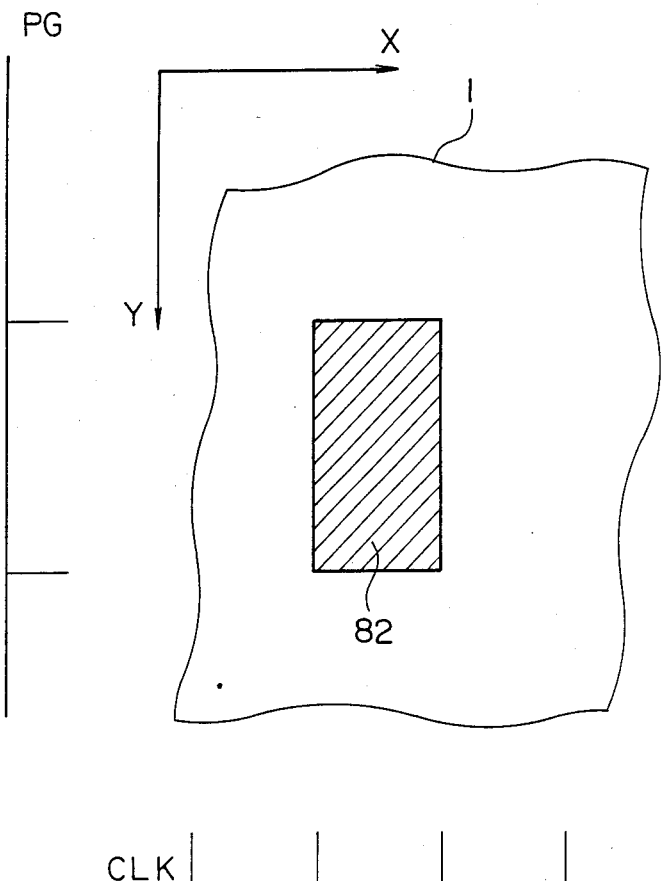
FIG. 15 is a diagram of assistance in explaining the minimum processing unit of a discriminating type flaw detector.

In the flaw data acquisition circuit having the aforementioned construction, the data obtained through the processing of the OR unit 72 is transferred as the minimum processing unit to the information processing device 17 via the FIFO memory 75. A region on the glass plate 1 corresponding to this minimum processing unit is shown by numeral 82 in FIG. 15. That is, the region constituting the minimum processing unit corresponds to a pulse interval of clocks CLK in the X-axis direction, and to a pulse interval of the frequency-divided line synchronization signal PG in the Y-axis direction.

With such a method, however, a plurality of flaw data could be output for a single flaw in a glass plate from the OR unit, and as a result, the information processing device 17 has to process a plurality of flaw data for a single flaw. This could result in an increased burden on the software processing of the information processing device.

When a single flaw is scanned by the laser beam spot, the flaw data $D_{11}$, $D_{12}$, $-D_{52}$ output by the flaw data generating circuit 14 based on changes in the quantity of light detected by each light receptor are not always output at the same timing. In such a case, the flaw data having shifted generation timings could be identified as the flaw data for a single flaw.

Figure 16:
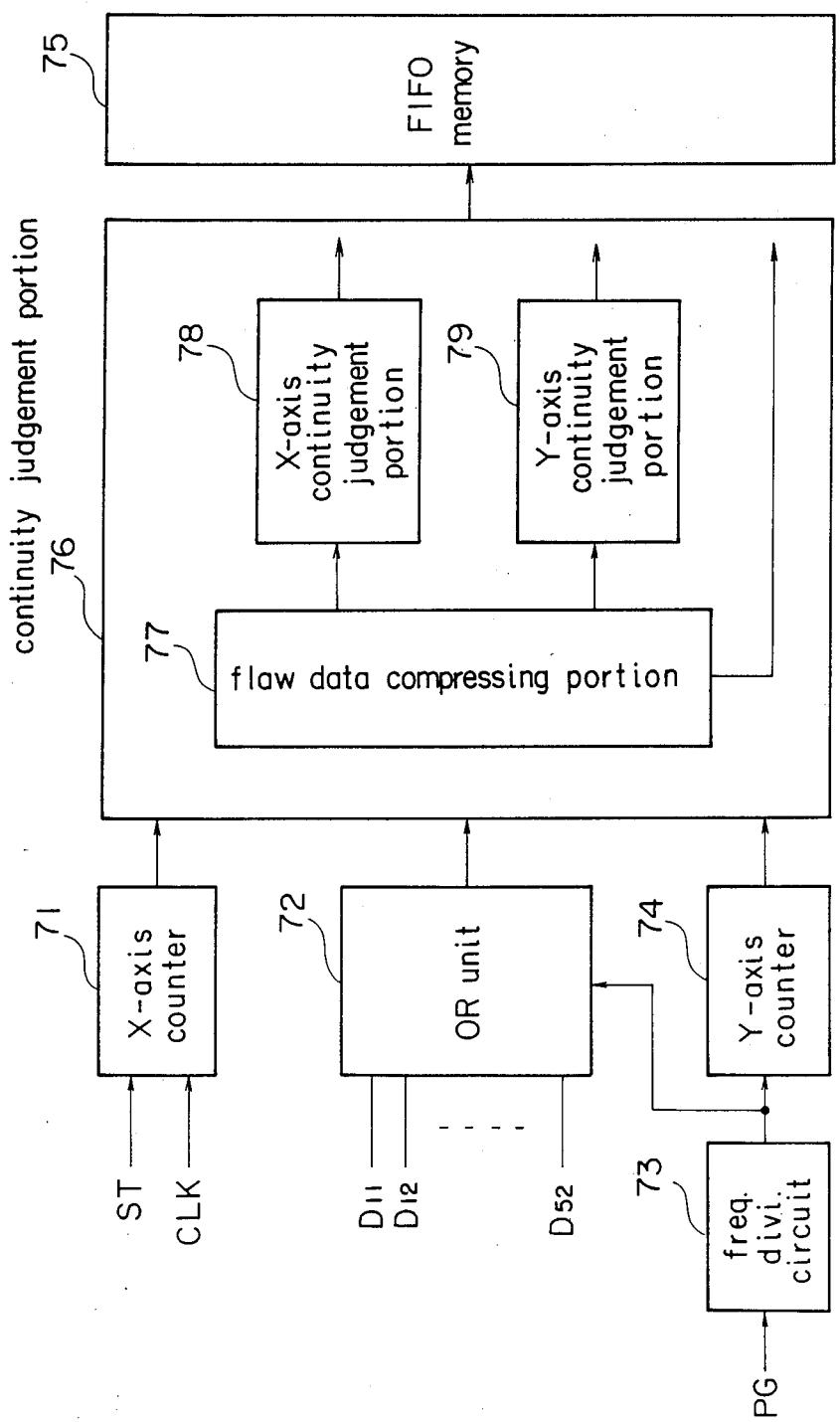
FIG. 16 is a block diagram illustrating another example of the flaw data acquisition circuit.

An example of the flaw data acquisition circuit designed to overcome this problem is shown in FIG. 16. This flaw data acquisition circuit is the same as the flaw data acquisition circuit shown in FIG. 11, except that a continuity judgment portion 76 is added to the succeeding stage of the X-axis counter 71, OR unit 72 and Y-axis counter 74 thereof.

The continuity judgment portion 76 comprises a flaw data compressing portion 77 which compresses flaw data from the OR unit 72, an X-axis continuity judgment portion 78 which judges the X-axis continuity of the compressed data and outputs a start address and an end address in the X-axis direction, and a Y-axis continuity judgment portion 79 which judges the Y-axis continuity of the compressed data and outputs a start address and an end address in the Y-axis direction.

Figure 17:
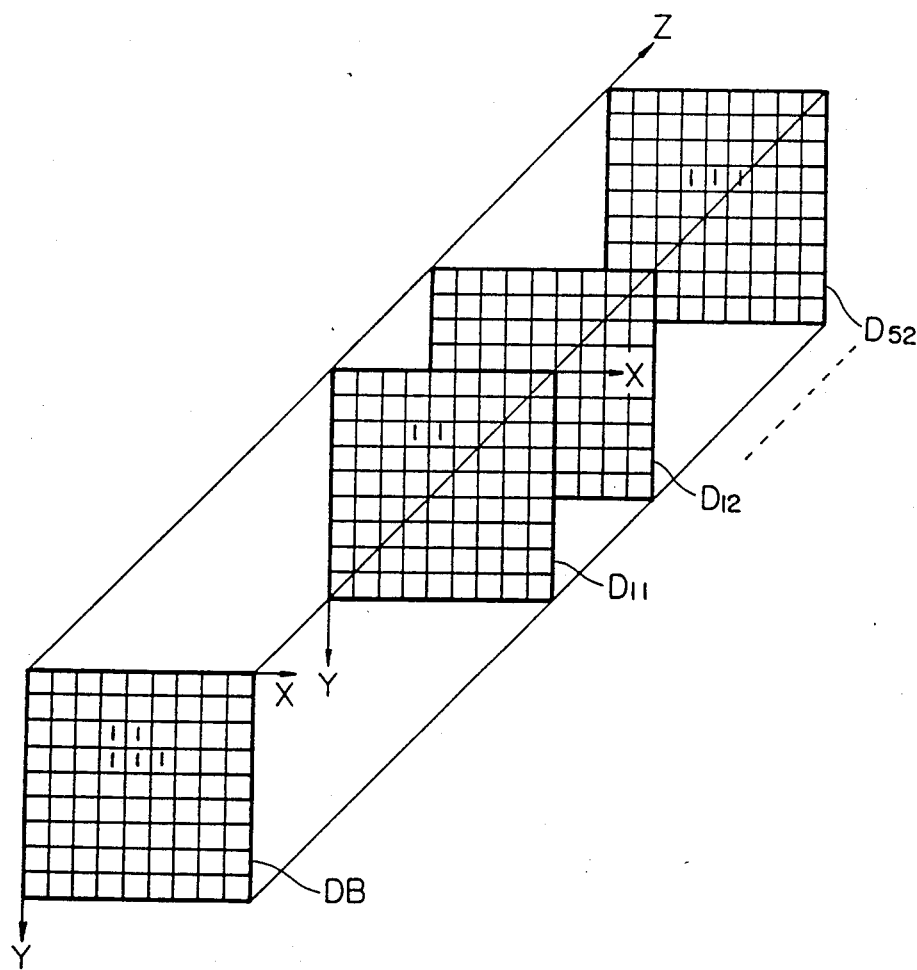
FIGS. 17, 18A and 18B are diagrams of assistance in explaining the operation of a continuity judgement portion.
Figure 18A:
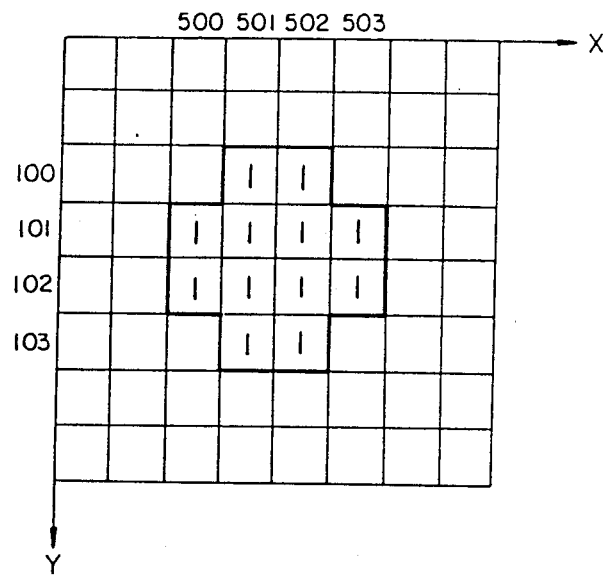
Figure 18B:
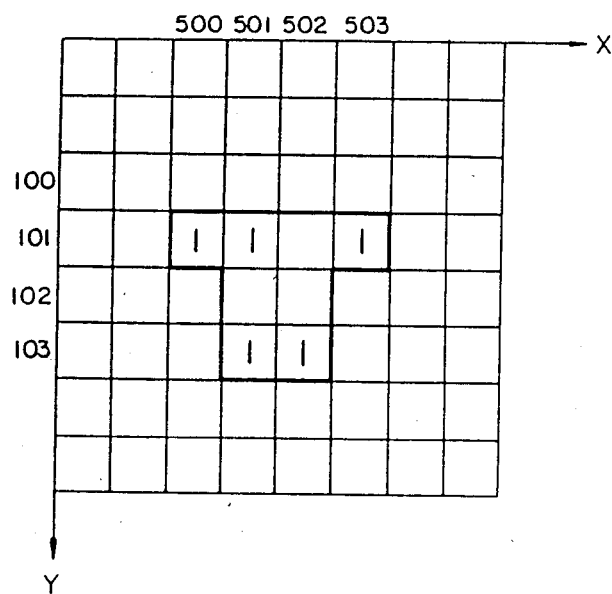

The operation of the continuity judgment portion 76 having the abovementioned construction will be described, referring to FIGS. 17, 18A and 18B FIG. 17 is a schematic diagram of assistance in explaining the operation of the flaw data compressing portion 77 which compresses flaw data. FIGS. 18A and 18B are diagrams illustrating bit patterns of the compressed flaw data to explain the operation of the X-axis continuity judgment portion 78 and the Y-axis continuity judgment portion 79.

As type-wise flaw data $D_{11}$, $D_{12}$,-$D_{52}$ are output by the OR unit 72, the flaw data for each type has a two-dimensional bit pattern in the X-axis address and Y-axis address directions. Assuming a three-dimensional space where the two-dimensionally arranged flaw data $D_{11}$, $D_{12}$,-$D_{52}$ are arranged in the Z-axis direction, it might be thought that three-dimensional flaw data groups $D_{11}$, $D_{12}$,-$D_{52}$ are output from the OR unit 72. The flaw data compressing portion 77 forms a compressed two-dimensional flaw data DB by ORing in the Z-axis direction the entire three-dimensional flaw data groups $D_{11}$, $D_{12}$,-$D_{52}$ arranged in the X-axis and Y-axis addresses. In FIG. 17, "1" bits are present only in the flaw data $D_{11}$ and the flaw data $D_{52}$.

FIGS. 18A and 18B show examples of the bit patterns of the flaw data compressed based on the following concept.

The X-axis continuity judgment portion 78 and the Y-axis continuity judgment portion 79 check the continuity of "1" bits in the X-axis and Y-axis directions, respectively, and check the presence or absence of a discontinuity in "1" bits. Based on parameters, both portions 78 and 79 determine whether the detected discontinuity be combined in the X-axis direction or in the Y-axis direction.

FIG. 18A shows a flaw data block synthesized by a continuity judgment process when all the parameters of the X-axis continuity judgment portion 78 and the Y-axis continuity judgment portion 79 are zero. The X-axis continuity judgment portion 78 outputs the address 500 as an X-axis start address for this flaw data block and the address 503 as an X-axis end address, while the Y-axis continuity judgment portion 79 outputs the address 100 as a Y-axis start address for the flaw data block and the address 103 as a Y-axis end address.

FIG. 18B shows a flaw data block synthesized by a continuity judgment process when all the parameters of the X-axis continuity judgment portion 78 and the Y-axis continuity judgment portion 79 are 1. When the parameters are 1, even when there is a discontinuity in an address, the discontinuity is combined to form a flaw data block shown in the figure. In this case, the X-axis continuity judgment portion 78 outputs the address 500 as an X-axis start address for this flaw data block and the address 503 as an X-axis end address The Y-axis continuity judgment portion 79 outputs the address 101 as a Y-axis start address for the flaw data block and the address 103 as a Y-axis end address. By performing continuity judgment in which discontinuities in "1" bits are combined by interpolation, it is made possible to identify these flaw data as he flaw data for a single flaw even if such flaw data are generated from a plurality of light receptors at shifted timings when a single flaw is scanned by the laser beam spot.

The Y-axis continuity judgment portion 79 outputs "1" bits, which represent the type of the flaw data, as a flaw pattern to the FIFO memory 75, and both the X-axis continuity judgment portion 78 and the Y-axis continuity judgment portion 79 output the X-axis start and end addresses and the Y-axis start and end addresses of the flaw data block as flaw location data to the FIFO memory 75. The Y-axis continuity judgment portion 79 has a function of forcibly cutting the Y-axis continuity of "1" bits if the continuity extends beyond a predetermined length and out-putting a flaw pattern and location information to the FIFO memory 75.

The FIFO memory 75 stores these flaw patterns and location data fed by the X-axis and Y-axis continuity judgment portions 78 and 79 to transfer to the memory of the information processing device 17 by direct memory access.

With the aforementioned flaw data acquisition circuit processing time in the information processing device can be reduced substantially, compared with the conventional flaw data acquisition circuit having no continuity judgment circuit because the number of flaws processed by the information processing device can be matched with the actual number of flaws in a glass plate since the flaw data output by the OR unit are compressed, subjected to X-axis and Y-axis continuity judgment, and combined into a single flaw data block; and the flaw data and location data for the flaw data block are output to the FIFO memory. By carrying out continuity judgment, the flaw data from light receptors generated at shifted timings can be identified as the flaw data for a single flaw.

Figure 19:
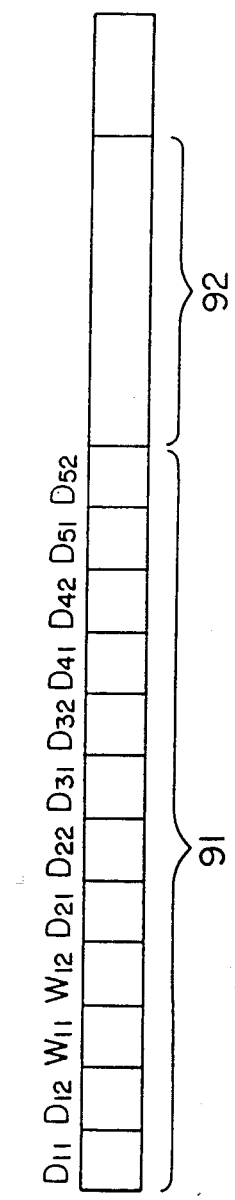
FIG. 19 is a diagram illustrating the format of the data output from the flaw data acquisition circuit.

FIG. 19 shows a format of the data transferred from the flaw data acquisition circuit 15 to the information processing device 17. This data consists of a flaw pattern 91 comprising a bit train representing the type and size of a single flaw in a glass plate, and location data 92 representing the location of the flaw.

As shown in FIG. 2, the information processing device 17 has a flaw discriminating pattern table 16 for judging the type, size, grade, etc. of a flaw, with which the flaw pattern fed from the flaw data acquisition circuit 15 to discriminate the type, size, grade, etc. of the flaw, and the location of the flaw from the location data fed from the flaw data acquisition circuit 15, and sends these discriminating results to a host information processing system, which in turn controls the manufacturing process and the sorting process based on the information supplied.

In the foregoing, a discriminating type flaw detector embodying this invention has been described, but the accuracy with which the type, size, etc. of a flaw are discriminated can be further improved based on the more detailed flaw data obtained by raising the detection level and width judgment level of the flaw data generating circuit by additionally providing a plurality of light receptors for detecting reflected and diffused light.

As noted earlier, flaws in a glass plate include a drip formed by deposition of tin in the tin bath in the manufacturing line on the surface of the glass plate, foreign matter remaining inside the glass plate, a knot formed by almost molten foreign matter remaining inside the glass plate in a shape with a streaming tail, and a bubble formed by an air bubble remaining inside the glass plate.

Unlike other flaws, a drip may increase in size in the so-called BTL process (where heated glass plates are bent and laminated under pressure) for manufacturing sandwich glass for automobiles. A drip of a size 0.2 mm×0.2 mm, for example, increases to a size of 0.5 mm×0.5 mm as a result of the BTL process. Consequently, it is necessary to detect drips of sizes over 0.2 mm×0.2 mm, for example, in the glass plate manufacturing process.

The conventional flaw detector relying on transmitted light for flaw detection, however, cannot discriminate drips of sizes over 0.2 mm×0.2 mm from other types of flaws of sizes over 0.2 mm×0.2 mm, resulting in deteriorated product yield.

The use of the discriminating type flaw detector of this invention can solve the aforementioned problems since it can identify and detect a flaw as a drip.

Figure 20:
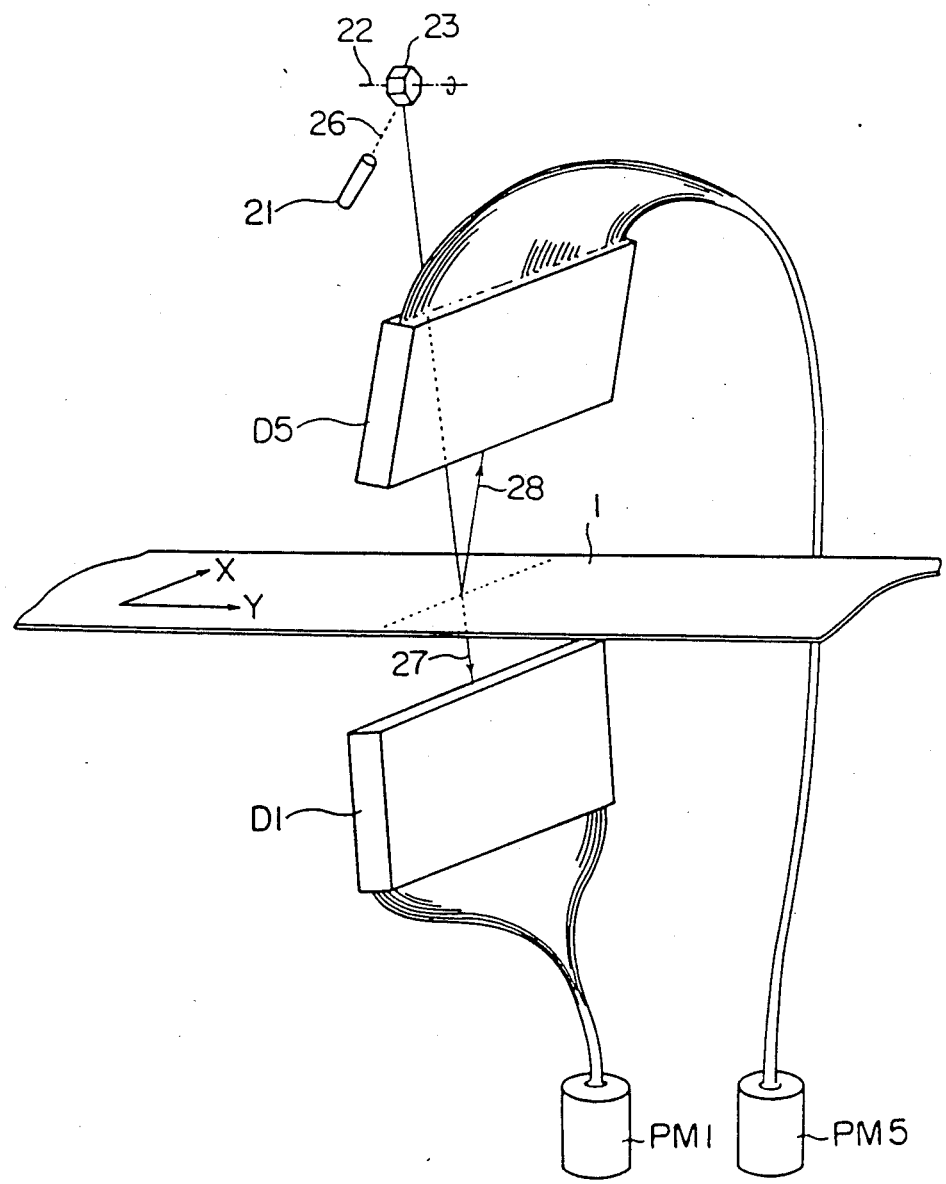
FIG. 20 is a perspective view of the flaw detector of a drip detecting device.

FIG. 20 is a perspective view of the flaw detector of a drip detecting device suitable for drip detection, which employs two light receptors; a light receptor D1 for transmitted light and a light receptor D5 for reflected light, and has the same construction as the flaw detector shown in FIG. 3 in other respects. Like parts are therefore indicated by like numerals shown in FIG. 3.

Figure 21:
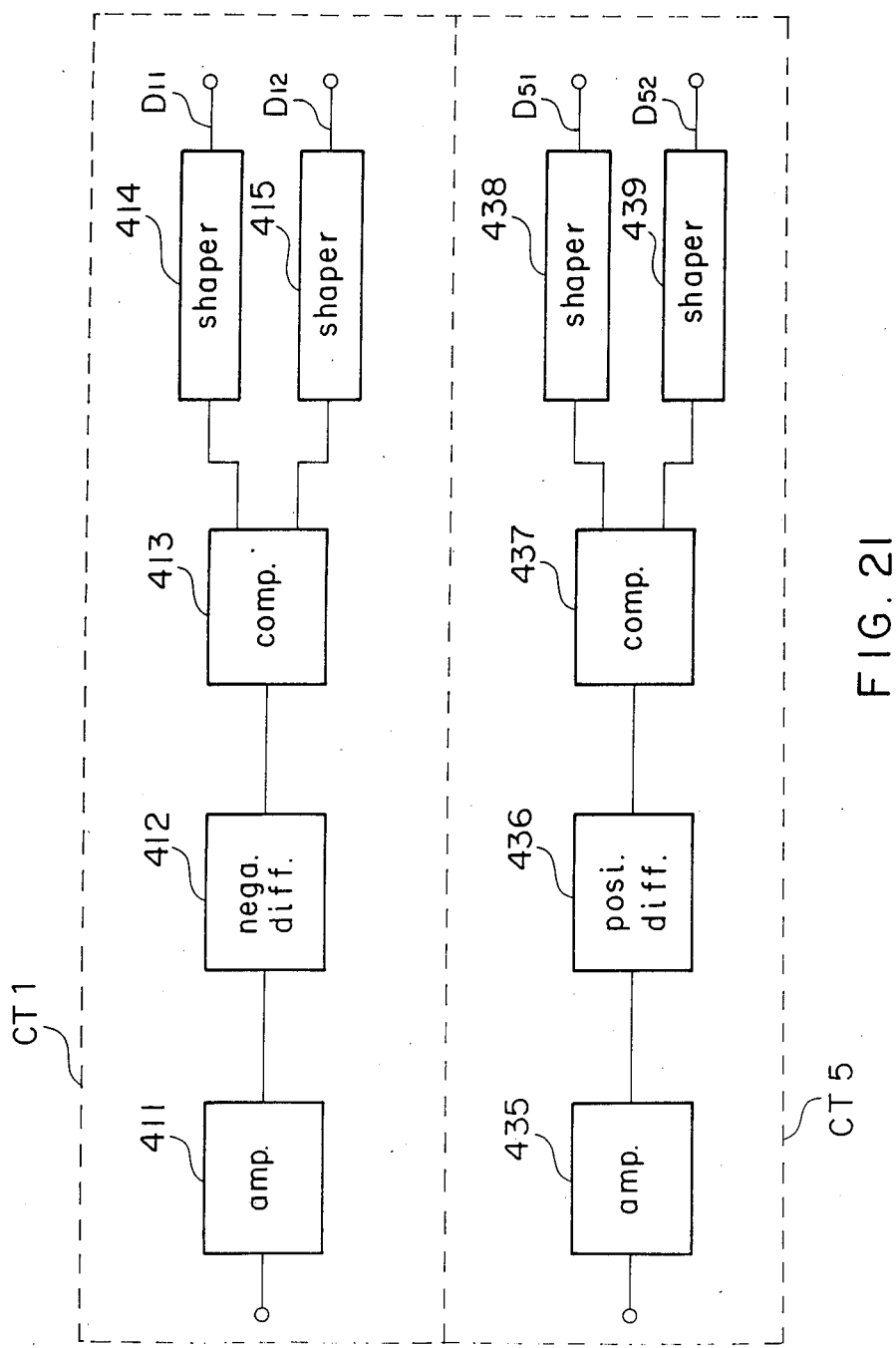
FIG. 21 is a block diagram of a flaw data generating circuit for drips.

A flaw data generating circuit generating flaw data containing information on the types and sizes of flaws by processing the electrical signals fed from photomultiplier tubes PM1 and PM5 comprises, as shown in FIG. 21, a flaw data generating portion CT1 for processing the electrical signals fed from a photomultiplier tube PM1, and a flaw data generating portion CT5 for processing the electrical signals fed from a photomultiplier tube PM5. In the figure, like parts are indicated by like numerals shown in FIG. 7. The flaw data generating portion CT1 shown in FIG. 21, however, does not carry out width judgment processing.

The flaw data $D_{11}$, $D_{12}$, $D_{51}$ and $D_{52}$ representing the types and sizes of flaws, output by this flaw data generating circuit, are processed in the same manner in the flaw data acquisition circuit as that described above.

The information processing device prestores a flaw discriminating pattern for judging the types and sizes of flaws, with which the flaw pattern fed from the flaw data acquisition circuit to discriminate the types and sizes of flaws.

When a flaw being detected is a drip, flaw data $D_{51}$ and $D_{52}$ exist in the flaw pattern, in addition to the flaw data $D_{11}$ and $D_{12}$, so the information processing device can identify the flaw as a drip by comparing the flaw pattern with the prestored flaw discriminating pattern table.

As described above, since this drip detecting device can detect changes in the quantity of reflected light, in addition to detection of the quantity of transmitted light, drips can be detected with high accuracy using a combination of these detection results.

Although the light receptors used in the aforementioned discriminating type flaw detectors employ optical fibers, variations tend to be caused in the waveforms of received light because of variability in the sensitivity of optical fibers, the fixing angle of the light-receiving ends of optical fibers, and the degree of polishing of the light-receiving end face of optical fibers.

Figure 22A:
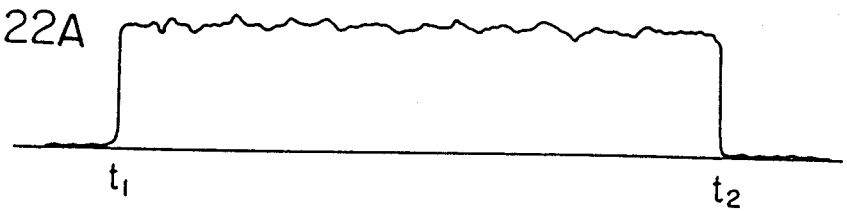
FIGS. 22A and 22B are diagrams illustrating the output waveforms of a light receptor.
Figure 22B:
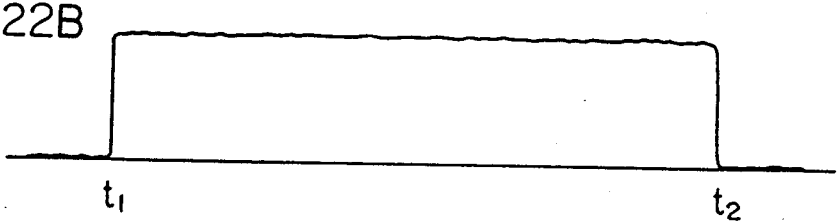

FIG. 22 (a) shows the waveform of the photoelectrically converted transmitted light received by the light receptor D1. As transmitted light always falls upon the light receptor D1, the transmitted light received during one scan assumes a waveform as shown in FIG. 22 (a) which rises from time $t_1$ to $t_2$. The actual waveform of the received light however, could assume an uneven waveform as shown in the figure when there are variations in the received light. In addition, although the light receptors $D2_A$, $D2_B$, $D3_A$, $D3_B$, $D4_A$ and $D4_B$, which output waveforms only when they receive transmitted and diffused light, the waveforms output by these light receptors tend to be uneven if there are variations in the received light. In this way, if the waveforms of the light received by light receptors are uneven, the light receptors cause partial variations in sensitivity.

To prevent such variations in sensitivity, it is desirable to install a light diffuse in front of the light-receiving surface of the light receptor.

Figure 23A:
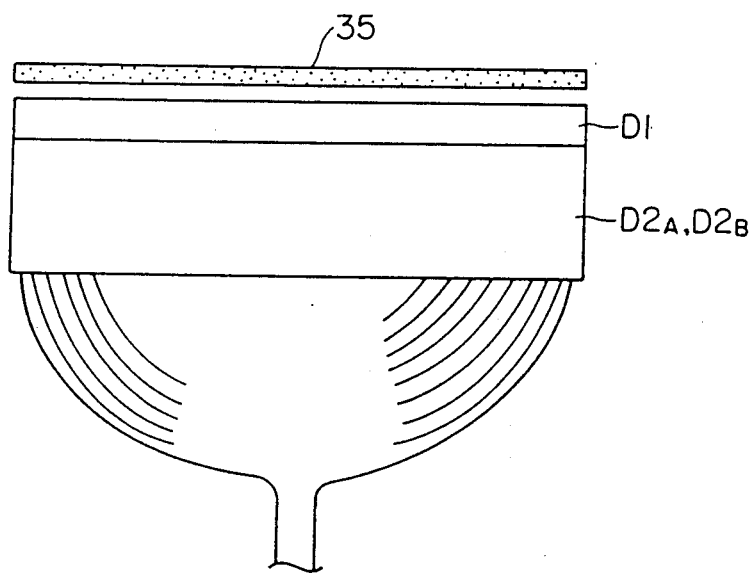
FIGS. 23A and 23B are diagrams illustrating a light receptor having a light diffuser.
Figure 23B:
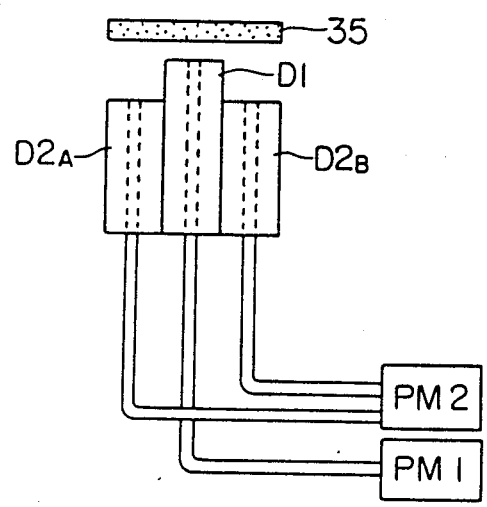

FIGS. 23A and 23B show the light receptor D1 and the light receptors $D2_A$ and $D2_B$, all having light diffusers. FIG. 23A is a front view and FIG. 23B is a side elevation. Each of these light receptors D1, $D2_A$ and $D2_B$ has a light diffuser 35 in front of the light-receiving surface thereof to diffuse light. The light diffuser may be made of any material that can diffuse light, such as ground glass plate. The light diffuser 35 is fixedly fitted to the light receptors D1, $D2_A$ and $D2_B$ by means of appropriate fixing members.

By using a light receptor having the aforementioned construction, the light falling upon the light diffuser 35, after diffused by the light diffuser 35, falls on the light-receiving surface of each light receptor. Since the diffused light falls upon the end faces of a plurality of optical fibers, and the light leaving the optical fibers is superposed on the photomultiplier tube, the photomultiplier tube outputs a waveform having no irregularities, and thus outputs a uniform waveform of the received light. The uniform output waveform of the photomultiplier tube PM1 is shown in FIG. 22 (b).

In the above embodiments, description has been made on the light receptor receiving the transmitted light and the most paraxial transmitted and diffused light. A similar light diffuser can be provided on each of the light receptors $D3_A$ and $D3_B$ receiving the paraxial transmitted and diffused light, and the light receptors $D4_A$ and $D4_B$ receiving the least paraxial transmitted and diffused light.

As described above, the discriminating type flaw detector having light receptors equipped with light diffusers can detect flaws with less variations in sensitivity and high accuracy.

Figure 24:
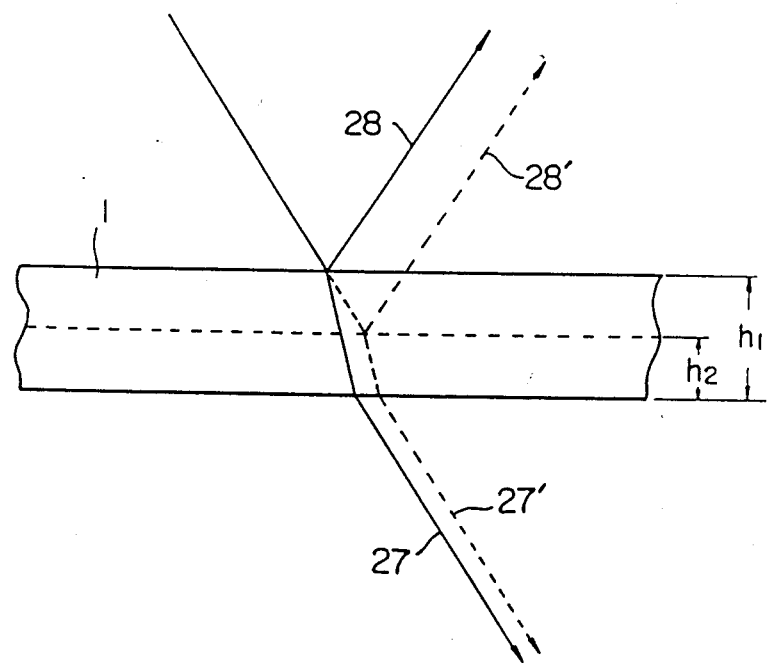
FIG. 24 is a diagram illustrating the shifted light paths of transmitted light and reflected light when the thickness of a glass plate changes.

In the discriminating type flaw detector of this invention, a laser beam falls upon a glass plate obliquely to avoid interference of laser beams, as noted earlier. When the thickness of a glass plate 1 changes from $h_1$ to $h_2$, therefore, the optical axis of the transmitted light 27 shown in FIG. 24 is shifted sideways, as shown by numeral 27', with the consequence that the optical axis of the reflected light 28 is also shifted as shown by numeral 28'. As a result, the light-receiving sensitivity of the light receptors not only for the transmitted light and the reflected light but also for the transmitted and diffused light is deteriorated. To prevent the light-receiving sensitivity of the discriminating type flaw detector from being deteriorated in this way, the discriminating type flaw detector shown in FIGS. 3 and 4 employs a rotatable parallel-mirror assembly 25 for thickness correction.

Now, a thickness correcting device having this parallel-mirror assembly 25 will be described.

Figure 25:
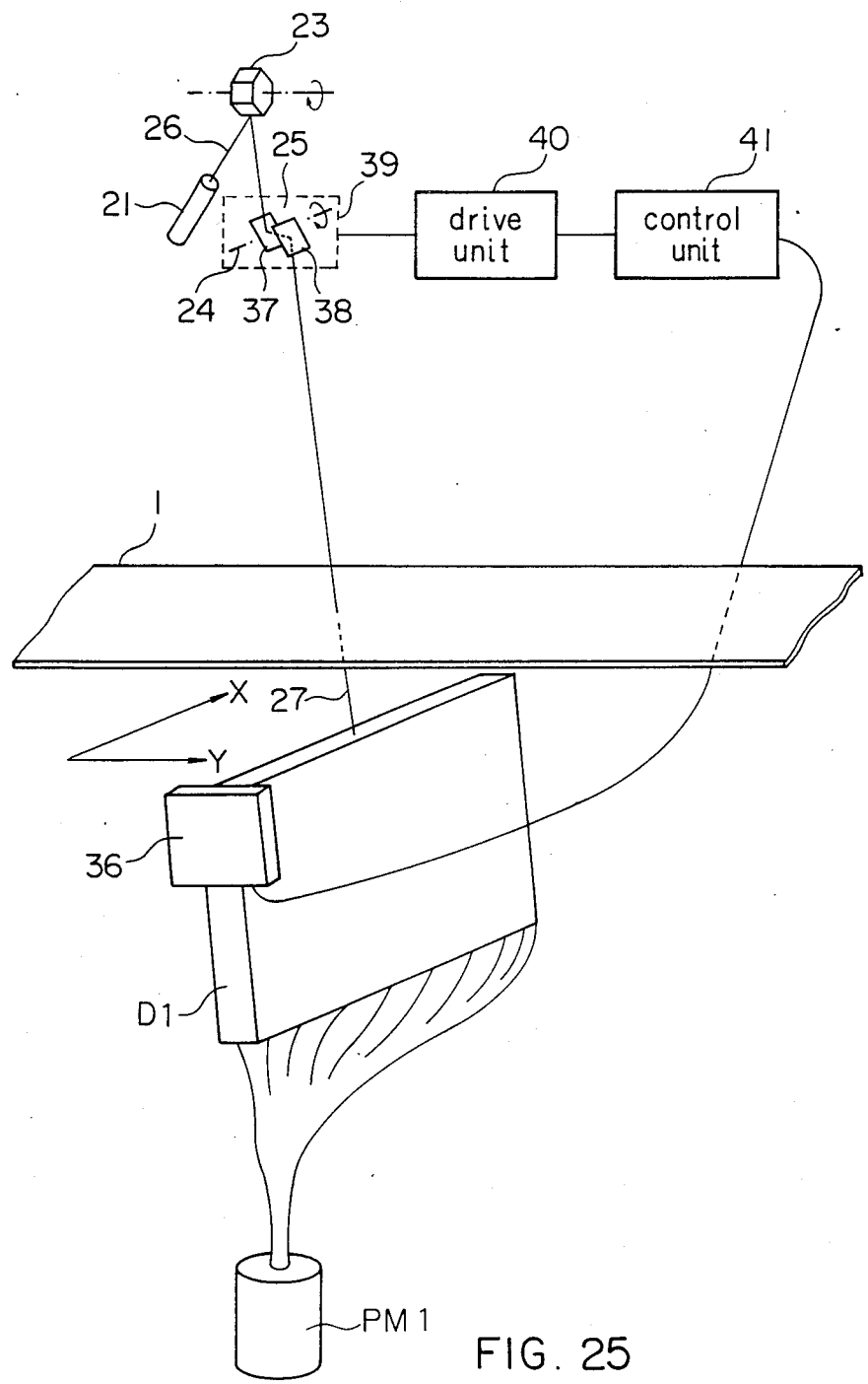
FIG. 25 is a diagram illustrating a first example of the thickness correcting device.

FIG. 25 shows a thickness correcting device for the transmitted light receptor and the transmitted and diffused light receptor, using a parallel-mirror assembly. In the figure, the transmitted and diffused light receptor is omitted.

According to this thickness correcting device, a CCD (charge-coupled device) camera 36 is provided at an end of the light-receiving surface of the transmitted light receptor D1, A parallel-mirror assembly 25 consisting of two parallel-opposing mirrors 37 and 38 is provided, which is rotatable around an axis 24 parallel with the X-axis and supported by a parallel-mirror assembly supporting mechanism 39. The parallel-mirror assembly 25 is rotated by a drive unit 40, such as a motor, which is controlled by a control unit 41 in which a location detection signal from the CCD camera 36.

Figure 26A:
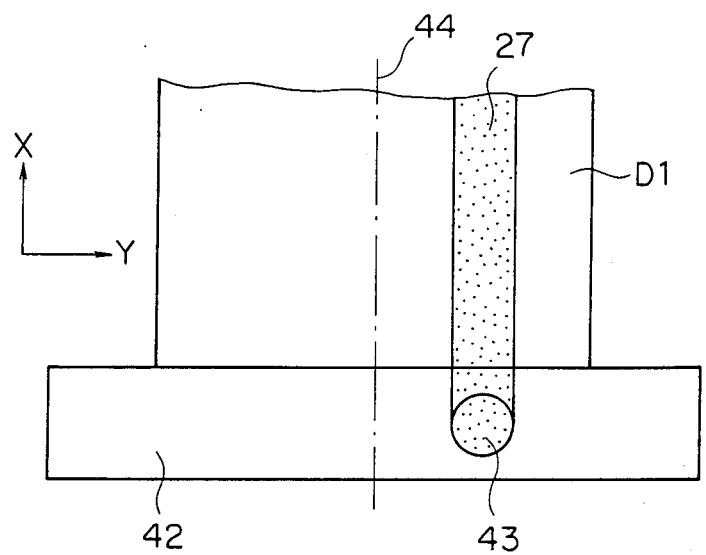
FIGS. 26A and 26B are diagrams of assistance in explaining the functions of a CCD camera for the thickness correcting device shown in FIG. 25.
Figure 26B:
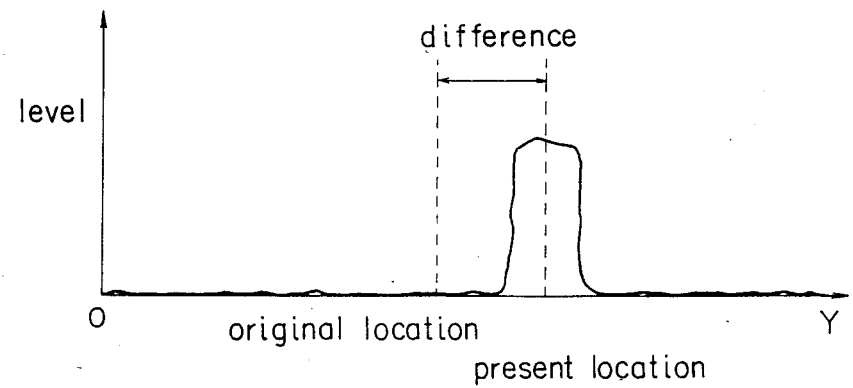

FIG. 26A is a diagram illustrating the light-receiving surface of the CCD camera 36, where a 1-dimensional line CCD sensor 42 of 1024 or 2048 bits is disposed in the Y-axis direction. Consequently, a light spot 43 falls on the 1-dimensional line CCD sensor 42, a location detection signal representing the location in the Y-axis direction of the incident light is output by the CCD camera 36. FIG. 26B shows a video signal as a location detection signal coming from the CCD camera 36, which indicates the present location of the incident light in the Y-axis direction. Assuming from the viewpoint of detection sensitivity that the location in the Y-axis direction at which the light is desired to fall on the light-receiving surface is an original location 44, the present location of the incident light is shifted from the original location 44.

Figure 27:
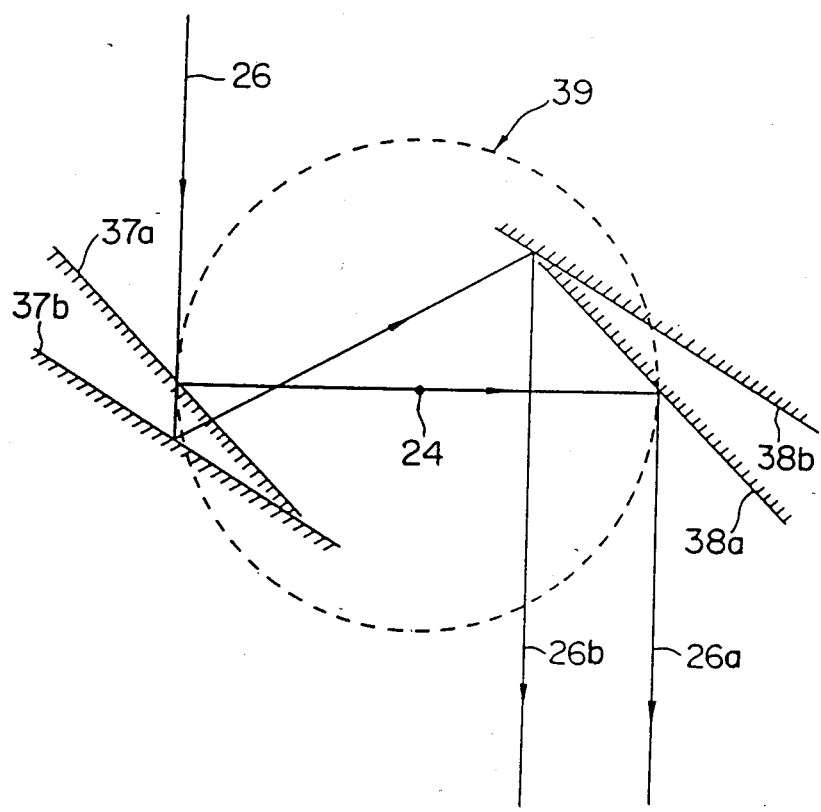
FIG. 27 is a diagram of assistance in explaining the functions of a parallel-mirror assembly for the thickness correcting device shown in FIG. 25.

FIG. 27 is a diagram of assistance in explaining the function of the parallel-mirror assembly in which two mirrors 37 and 38 are disposed in a parallelly opposing manner, and supported by a supporting mechanism 39 in such a rotatable fashion around the axis 24 while maintaining the relative locations thereof. Now, assume that the two mirrors 37 and 38 are disposed at locations 37a and 38a as shown in FIG. 27, a laser beam 26 from a rotating multiplanar mirror 23 is reflected by the mirror 37 and then by the mirror 38, and falls on a glass plate 1 along an optical axis 26a. When the parallel-mirror assembly 25 is rotated leftward from the above state to move the two mirrors to locations 37b and 38b, the laser beam 26 falling on the parallel-mirror assembly 25 comes out along an optical axis 26b. By rotating the parallel-mirror assembly 25 in this way, the path of the laser beam 26 falling on the glass plate 1 can be shifted. When the thickness of a glass plate 1 being inspected changes, therefore, the location at which the transmitted light 27 falls on the light receptor D1 can be corrected by rotating the parallel-mirror assembly 25.

In the thickness correcting device shown in FIG. 25, when the thickness of the glass plate 1 being inspected changes, the path of the transmitted light 27 is shifted, as described earlier. As the transmitted light whose path is shifted falls on the CCD camera 36, the CCD camera 36 detects the present location of the transmitted light 27 and enters the detection result to the control unit 41. The control unit 41 calculates the magnitude and direction of the shift of the present location of the transmitted light 27 from the original location, and controls the drive unit 40 to cause the parallel-mirror assembly 25 to rotate so that the transmitted light 27 falls on the original location of the light receptor D1.

Figure 28:
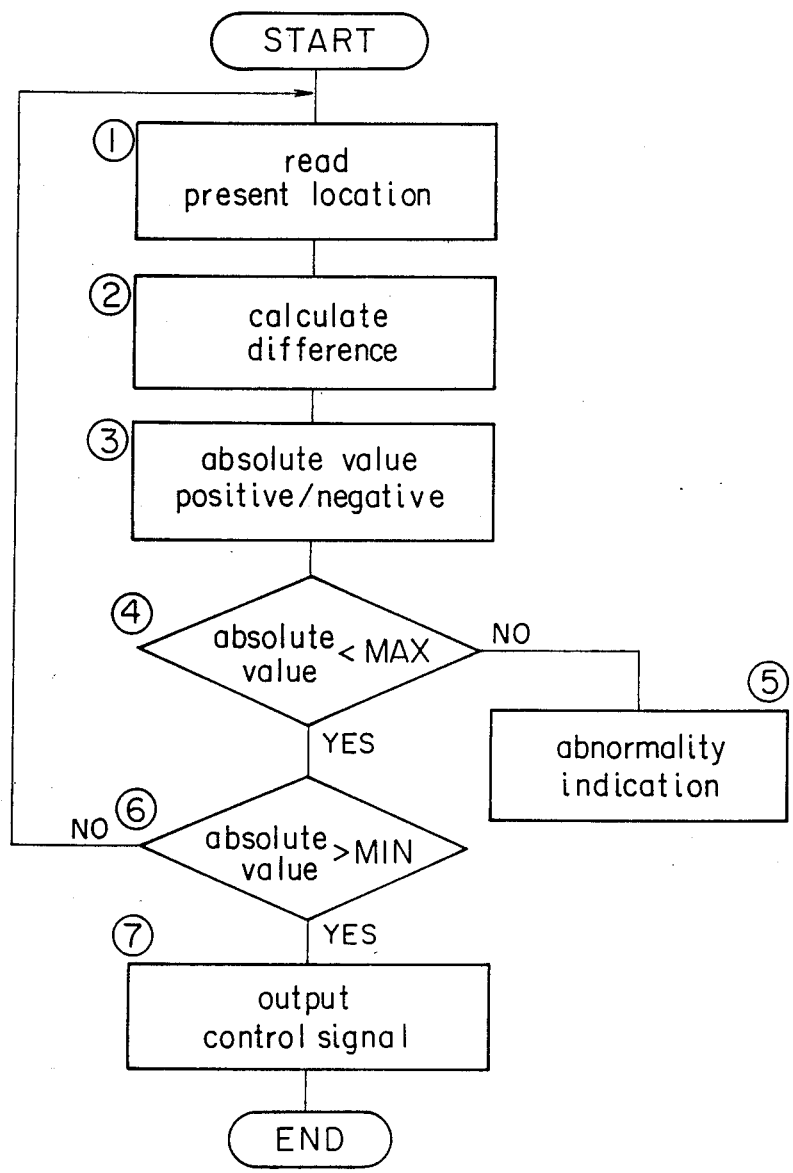
FIG. 28 is a flow chart of assistance in explaining the operation of a control unit for the thickness correcting device shown in FIG. 25.

The operation of the control unit 41 will be described in more detail, referring to a flow chart shown in FIG. 28. The control unit 41 reads the present location based on the location detection signal from the CCD camera 36 (STEP ①). Then, the control unit 41 calculates the difference between the present location and the original location (present location—original location) (STEP ②), and finds the absolute value of the difference while detecting the positive/negative sign thereof (STEP ③).

The positive difference indicates that the transmitted light 27 is shifted rightward from the original location 44, while the negative difference indicates that the transmitted light 27 is shifted leftward from the original location 44.

Next, the control unit 41 compares the absolute value of the difference with the maximum value (MAX) set in advance in the control unit 41 (STEP ④). If the absolute value of the difference is larger than the maximum value, the control unit 41 generates an abnormality indication, indicating that the CCD camera is defective, for example, and does not perform thickness correction (STEP ⑤). If the absolute value of the difference is smaller than the maximum value, the control unit 41 further compares the absolute value of the difference with the minimum value (MIN) (STEP ⑥). If the absolute value of the difference is smaller than the minimum value, the control unit 41 judges that the shift is too small to correct, and does not output any control signal, returning to STEP 1. If the absolute value of the difference is larger than the minimum value the control unit 41 outputs a control signal to the drive unit 40 (STEP ⑦). This control signal contains information on the absolute value of the difference, that is, the magnitude of the shift of the present location of the transmitted light 27 from the original location, and the positive/negative sign of the difference, that is, the direction in which the transmitted light is shifted with respect to the original location. The drive unit 40 rotates the parallel-mirror assembly 25 based on the control signal from the control unit 41 that so the transmitted light 27 falls upon the original location 44.

With the thickness correcting device of the aforementioned construction, the path of the transmitted light can be kept constant, even if the thickness of the glass plate changes, by providing a parallel-mirror assembly between the rotating multiplanar mirror and the glass plate, and rotating the parallel-mirror assembly to change the path of the laser beam falling on the glass plate. If the path of the transmitted light does not change the path of the transmitted and diffused light also does not change. Consequently, the light-receiving sensitivity of the transmitted light receptor and the transmitted and diffused light receptor does not deteriorate. Thus, the detection sensitivity of the discriminating type flaw detector can be kept at a high level.

Figure 29:
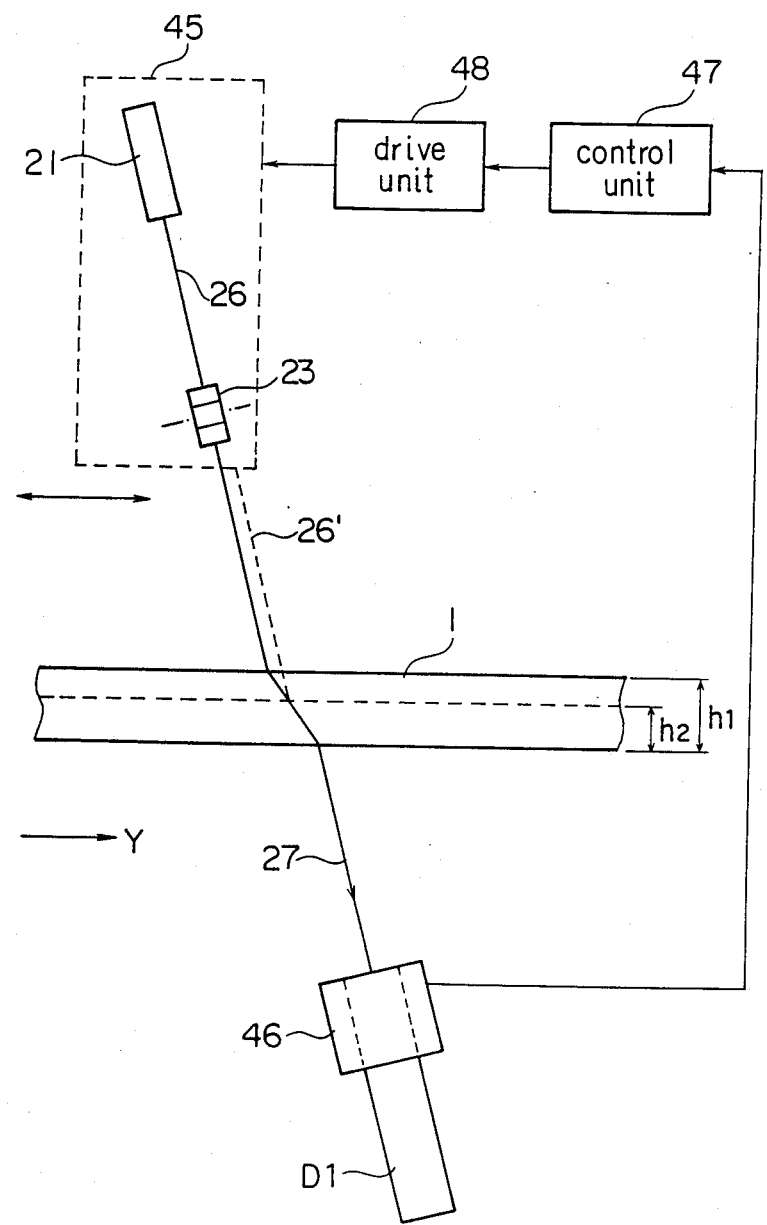
FIG. 29 is a diagram illustrating a second example of the thickness correcting device.

Although the foregoing description is concerned with the thickness correcting device using a parallel-mirror assembly, the same effect can be achieved by moving a light projector consisting of a laser source and a rotating multiplanar mirror, instead of using a parallel-mirror assembly. FIG. 29 shows a thickness correcting device based on this principle. A light projector having a laser source 21 and a rotating multiplanar mirror 23 is supported as a unit by a light projector supporting mechanism 45 which can move in parallel with the Y-axis. As in the case of the thickness correcting device shown in FIG. 25, this thickness correcting device comprises a CCD camera 46 provided at the end of the light receptor D1, a control unit 47 for outputting a control signal based on the transmitted light detecting location signal from the CCD camera 46, and a drive unit 48 for driving the supporting mechanism 45 based on the control signal from the control unit 47. The operation of these elements is similar to that of the thickness correcting device shown in FIG. 25. When the thickness of a glass plate 1 changes from $h_1$ to $h_2$, as shown in the figure, the entire light projector is moved in the Y-axis direction so that the incident light 26 falls on the glass plate 1 along the light path shown by a dotted line 26'.

Figure 30:
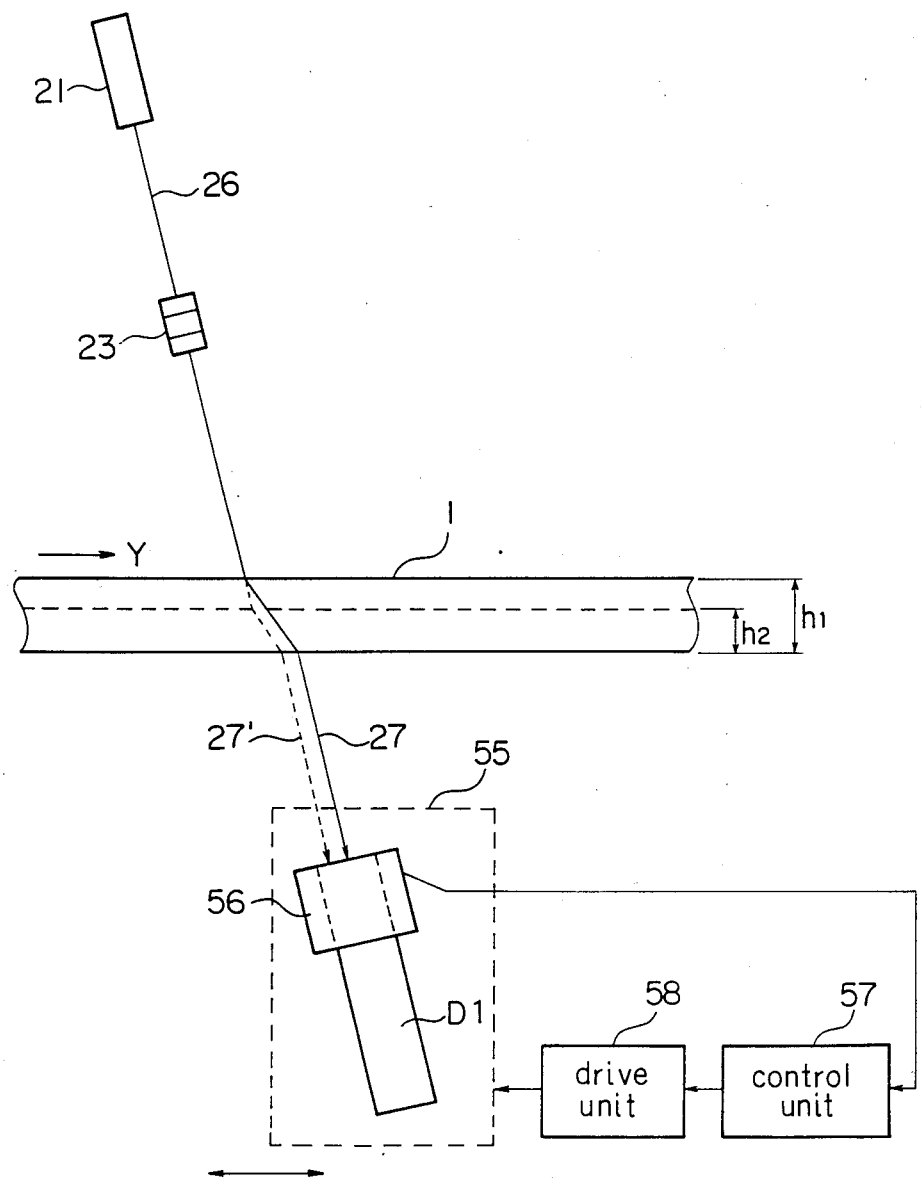
FIG. 30 is a diagram illustrating a third example of the thickness correcting device.

Although the light projector is moved in the above thickness correcting device, the light receptor may be moved, instead. FIG. 30 shows a thickness correcting device based on this principle. In the figure, the light receptor for the transmitted and diffused light is omitted to avoid ambiguity.

A transmitted light receptor and a transmitted and diffused light receptor are supported as a unit by a light receptor supporting mechanism 55 which can move in parallel with the Y-axis. This thickness correcting device comprises a CCD camera 56 provided at the end of a light receptor D1 and a control unit 57 outputting a control signal based on the transmitted light detecting location signal from the CCD camera, and a drive unit 58 for driving the supporting mechanism 55. The operation of these elements is the same as those of the thickness correcting devices shown in FIGS. 25 and 29. When the thickness of a glass plate 1 changes from $h_1$ to $h_2$ as shown in the figure, and the path of the transmitted light 27 changes as shown by a dotted line 27', the entire light receptor is moved in the Y-axis direction by the drive unit 58 so that the transmitted light falls on the original location of the light receptor D1.

Figure 31:
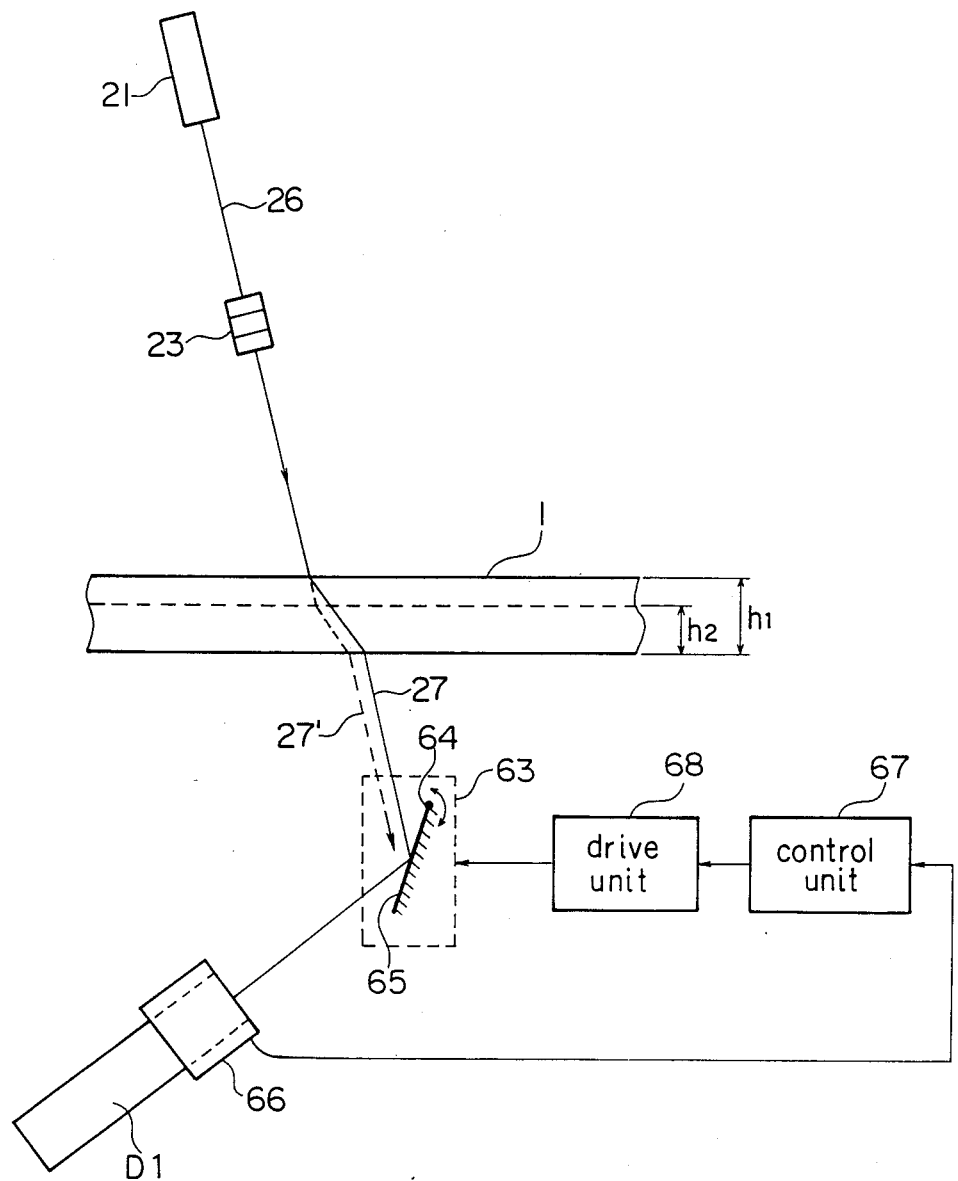
FIG. 31 is a diagram illustrating a fourth example of the thickness correcting device.

Although the light receptor itself is moved in this thickness correcting device, a rotatable light-path changing mirror may be provided between the light receptor and the glass plate, with the light receptor kept stationary, so that the light path can be changed by rotating the mirror. FIG. 31 shows a thickness correcting device based on this principle. In the figure, the transmitted and diffused light receptor is omitted. A mirror 65 that can be rotated around an axis parallel with the X-axis is provided in the path of the transmitted light and the transmitted and diffused light coming from a glass plate 1 to reflect these light beams to change the path thereof. A light receptor is provided in the path of the light reflected by the mirror 65. A light-path changing mirror 65 is rotatably supported by the supporting mechanism 63.

Like the abovementioned thickness correcting devices, this thickness correcting device comprises a CCD camera 66 provided at the end of a light receptor D1, a control unit 67 for outputting a control signal based on the transmitted light detecting location signal varied from the CCD camera, and a drive unit 68 for rotating a light-path changing mirror 65 based on the control signal fed from the control unit 67. The operation of these elements is the same as those of the abovementioned thickness correcting devices. As the thickness of a glass plate 1 changes from $h_1$ to $h_2$ as shown in the figure, and the path of the transmitted light 27 changes as shown by a dotted line 27', the light-path changing mirror 65 is rotated by the drive unit 68 so that the transmitted light falls on the original location of the light receptor D1.

Figure 32:
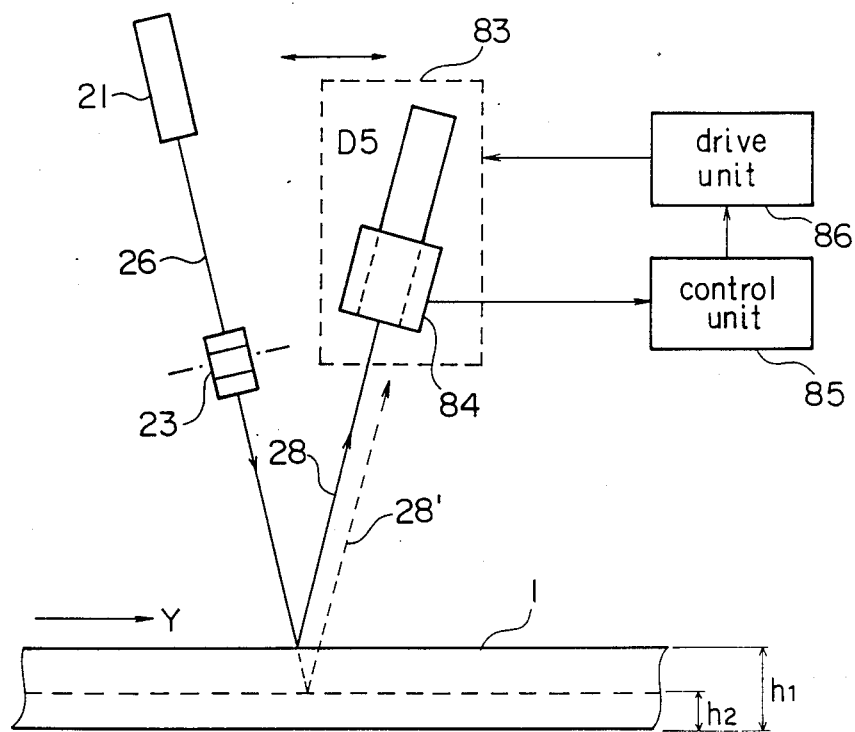
FIG. 32 is a diagram illustrating a fifth example of the thickness correcting device.

Although the abovementioned thickness correcting devices are for correcting glass plate thickness for the transmitted light receptor and the transmitted and diffused light receptor, thickness correction must be performed for the reflected light receptor. FIG. 32 is a diagram illustrating a thickness correcting device for this purpose. This thickness correcting device comprises a light receptor D5 for receiving reflected light 28 supported by a supporting mechanism 83 that can be moved in parallel with the Y-axis, a CCD camera 84 provided at the end of the light receptor D5, a control unit 85 for outputting a control signal based on the reflected light detecting location signal fed from the CCD camera 84, and a drive unite 86 for driving a supporting mechanism 83 based on the control signal from the control unit 85. The operation of these elements is the same as those of the aforementioned thickness correcting devices. As the thickness of a glass plate 1 changes from $h_1$ to $h_2$ as shown in the figure, and the path of the reflected light changes as shown by a dotted line 28', the light receptor D5 is moved in the Y-axis direction by the drive unit 86 so that the reflected light falls on the original location of the light receptor D5.

Figure 33A:
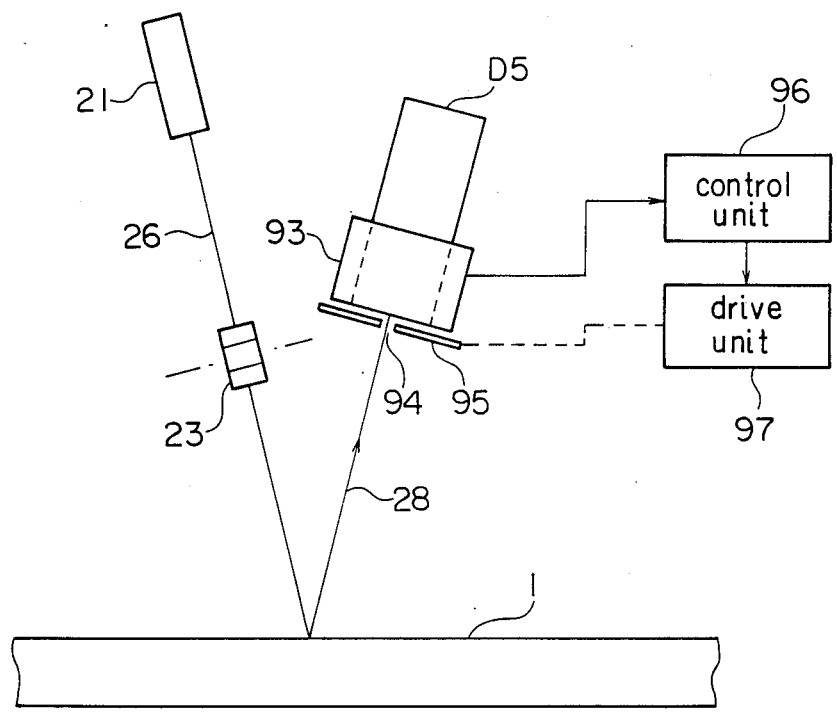
FIGS. 33A and 33B are diagrams illustrating a sixth example of the thickness correcting device.
Figure 33B:
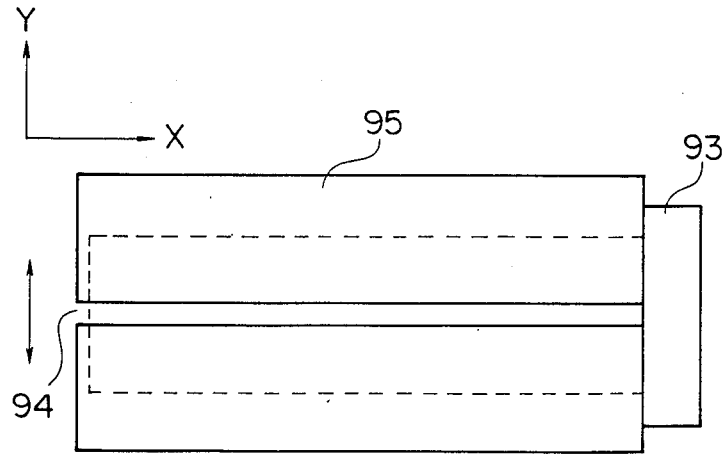

Although this thickness correcting device employs a light receptor D5 of an optical fiber type having an extremely slender light-receiving surface, the use of such an optical fiber type light receptor is inevitable in light receptors for transmitted light and transmitted and diffused light which have to be disposed in close proximity from considerations of the effective light-receiving angle. A light receptor for reflected light, on the other hand, may use a diffuser box (condenser box) having a wide light-receiving surface. A thickness correcting device using such a diffuser box is shown in FIGS. 33A and 33B.

This thickness correcting device has a CCD camera 93 at the end of a diffuser box type reflected light receptor D5, and a mask 95 with a slit 94 extending in the X-axis direction is provided in front of the light receptor D5. This mask is supported in such a manner that the mask can move in parallel with the front surface of the light receptor D5 in the direction normal to the X-axis direction. FIG. 33A is a diagram showing the light receptor D5 viewed from the X-axis direction, and FIG. 33B is a diagram showing the light receptor D5 viewed from the mask.

As in the case of the aforementioned thickness correcting devices, this thickness correcting device has a control unit 96 for outputting a control signal based on the reflected light detecting location signal fed from a CCD camera 93, and a drive unit 97 for driving a mask 95 based on the control signal from the control unit 96.

With this thickness correcting device, a CCD camera 93 detects the location at which reflected light 28 falls on a light receptor D5 and sends a present location detecting signal to a control unit 96. The control unit 96 controls a drive unit 97 to move a mask 95 so that the reflected light 28 impinges on the light receptor D5 through a slit 94 of the mask 95. Consequently, even when the path of the reflected light 28 is shifted with a change in the thickness of a glass plate 1, the reflected light can reach the light receptor as the mask is moved in accordance with the shift of the light path.

Although this thickness correcting device uses the slit of the mask to collect the reflected light, another arrangement can be adopted to collect only reflected and diffused light.

In the foregoing, description has been made on each example of the thickness correcting device. Means for detecting the location at which transmitted light or reflected light falls on a light receptor need not be lifted to a CCD camera, but other location detecting means may be employed.

In the discriminating type flaw detector of this invention, when light transmittance changes in accordance with the thickness, color, etc. of a light-transmitting plate material being inspected, a glass plate, for example, or the output of a laser source changes, or the sensitivity of a photomultiplier tube deteriorates, it is necessary to keep detection sensitivity at a constant level to maintain the accuracy of flaw detection. A method to attain this is the automatic control of the sensitivity, or gain of the photomultiplier tube. In this case, transmitted light and reflected light fall on light receptors D1 and D5 at all times during one scan, regardless of the presence or absence of a flaw in a glass plate, and an electrical signal is always output by photomultiplier tubes PM1 and PM5. It is easy therefore to detect the level of an electrical signal portion not corresponding to a flaw to perform automatic gain control (AGC) so as to keep the signal level constant. However, a specially designed AGC device is required to perform the automatic control of the sensitivity of these photomultiplier tubes because light receptors $D2_A$ and $D2_B$ for detecting the most paraxial transmitted and diffused light, light receptors $D3_A$ and $D3_B$ for detecting paraxial transmitted and diffused light and light receptors $D4_A$ and $D4_B$ for detecting the least paraxial transmitted and diffused light receive transmitted and diffused light only when there is a flaw in a glass plate, and accordingly photomultiplier tubes PM2, PM3 and PM4 output electrical signals only in such an occasion.

Figure 34A:
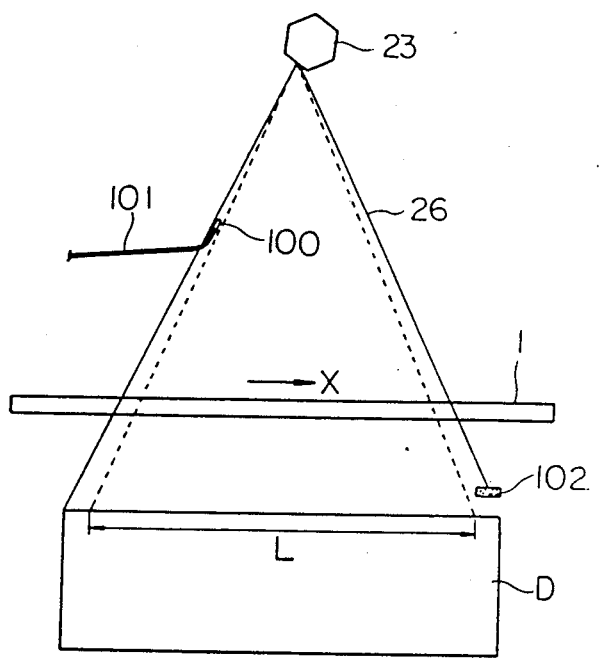
FIGS. 34A and 34B are diagrams of a first example of the AGC device.
Figure 34B:
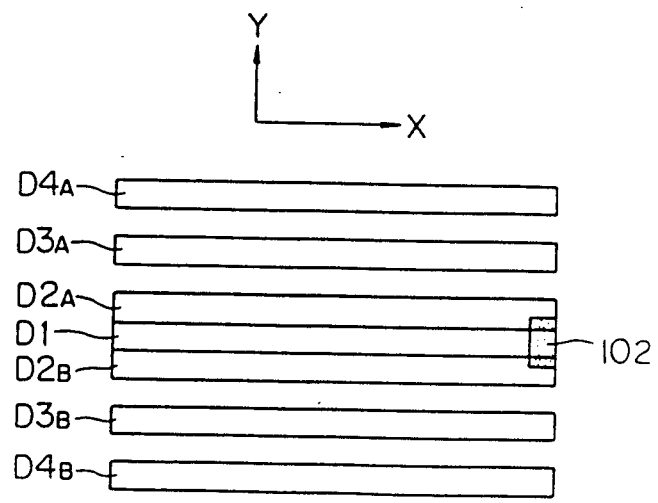

FIGS. 34A, 34B, 35, and 36 are diagrams illustrating an example of such an AGC device. FIGS. 34A and 34B show the light receptor portion of light receptors D1, $D2_A$, $D2_B$, $D3_A$, $D3_B$, $D4_A$ and $D4_B$ of the AGC device for receiving transmitted light and transmitted and diffused light; FIG. 34A being a diagram showing the light receptor portion viewed from the Y-axis direction, and FIG. 34B being a diagram showing the light receptor portion viewed from the side of the light-receiving surface. In FIG. 34A, a light receptor is typically shown by numeral D. In the figure, numeral 23 refers to a rotating multiplanar mirror; 26 to a laser beam; 100 and 101 to a light receptor and an optical fiber, respectively, for a start pulse ST. The laser source and the parallel-mirror assembly are omitted in the figure.

This AGC device has a light diffusion plate 102, made of ground glass, located above the area near an end in the longitudinal direction of a light receptor D1, below a glass plate being inspected, and outside an effective scanning range L.

As transmitted light, which falls on the light receptor D1 at all times during one scan, impinges on the light diffusion plate 102, the diffused light falls on the light receptors $D2_A$, $D2_B$, $D3_A$, $D3_B$, $D4_A$ and $D4_B$. The light collected for the purpose of AGC is hereinafter referred to as reference light.

FIG. 35 is a diagram illustrating the electrical circuit portion of this AGC device. Typically, an electrical circuit portion for a photomultiplier tube PM2 converting the most paraxial transmitted and diffused light received light receptors $D2_A$ and $D2_B$ will be described in the following. This electrical circuit portion comprises a sampling circuit 103 for sampling an electrical signal corresponding to the reference light from the photomultiplier tube PM2, a hold circuit 104 for holding a sampled value, a control circuit 105 for controlling a high-voltage generating circuit 106 for supplying a voltage to be applied to the photomultiplier tube PM2 based on the sampled value from the hold circuit.

Next, the operation of this AGC device will be described, referring to a signal waveform diagram shown in FIG. 36.

In FIG. 34A, it is assumed that a light spot scans a glass plate 1 from left to right in the X-axis direction. As the light impinges on the light diffusion plate 102, reference light falls on the most paraxial transmitted and diffused light receptors $D2_A$ and $D2_B$. The reference light is fed to the photomultiplier tube PM2 and converted to a reference light signal RS. FIG. 36 (a) shows the reference light signal RS contained in an output signal from the photomultiplier tube PM2. The level of the reference light signal RS is dependent on the light transmittance of the glass plate 1, the change in the output of the laser source, and the sensitivity of the photomultiplier tube. The electrical signal from the photomultiplier tube PM2 is fed to both a flaw data generating circuit and the sampling circuit 103.

In the sampling circuit 103, the abovementioned start pulse ST indicating the start of scanning, and the same clock CLK as a clock CLK input to the X-axis counter in a flaw data acquisition circuit are input. The start pulse ST is shown in FIG. 36 (b), and the clock CLK in FIG. 36 (c). The reference light signal RS is produced during a period other than the effective scanning period starting from the time of generation of the start pulse ST. In the sampling circuit 103, the clock CLK is counted based on the start pulse ST, and the reference light signal RS is sampled using a predetermined clock CLK as a sampling pulse. The sampled value is held in the hold circuit 104. The sampled value held in the hold circuit 104 is input in the control circuit 105. In the control circuit 105, the sensitivity of the photomultiplier tube PM2 is adjusted by comparing the sampled value with the standard level and controlling the voltage generated in the high-voltage generating circuit 106 and applied to the photomultiplier tube PM2 so that the level of the reference light signal RS is kept at a predetermined level at all times.

With the AGC device described above, The detection sensitivity of the discriminating type flaw detector is kept constant by providing a light diffuser at the end of the light receptor, causing the reference light to fall on the transmitted and diffused light receptor, and controlling the sensitivity of the photomultiplier tube so that the level of the reference light is kept at a predetermined level.

In the abovementioned AGC device, a light diffuser is provided below a glass plate being inspected, but the light diffuser may be provided above the glass plate, or on the side at which a light spot begins scanning.

Figure 37A:
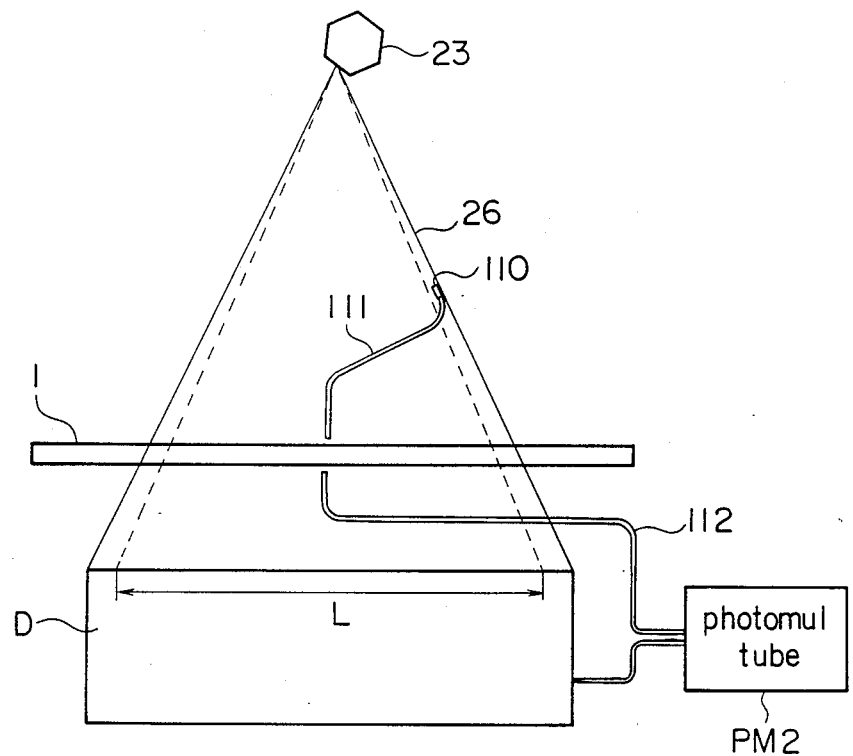
FIGS. 37A and 37B are diagrams illustrating a second example of the AGC device.
Figure 37B:
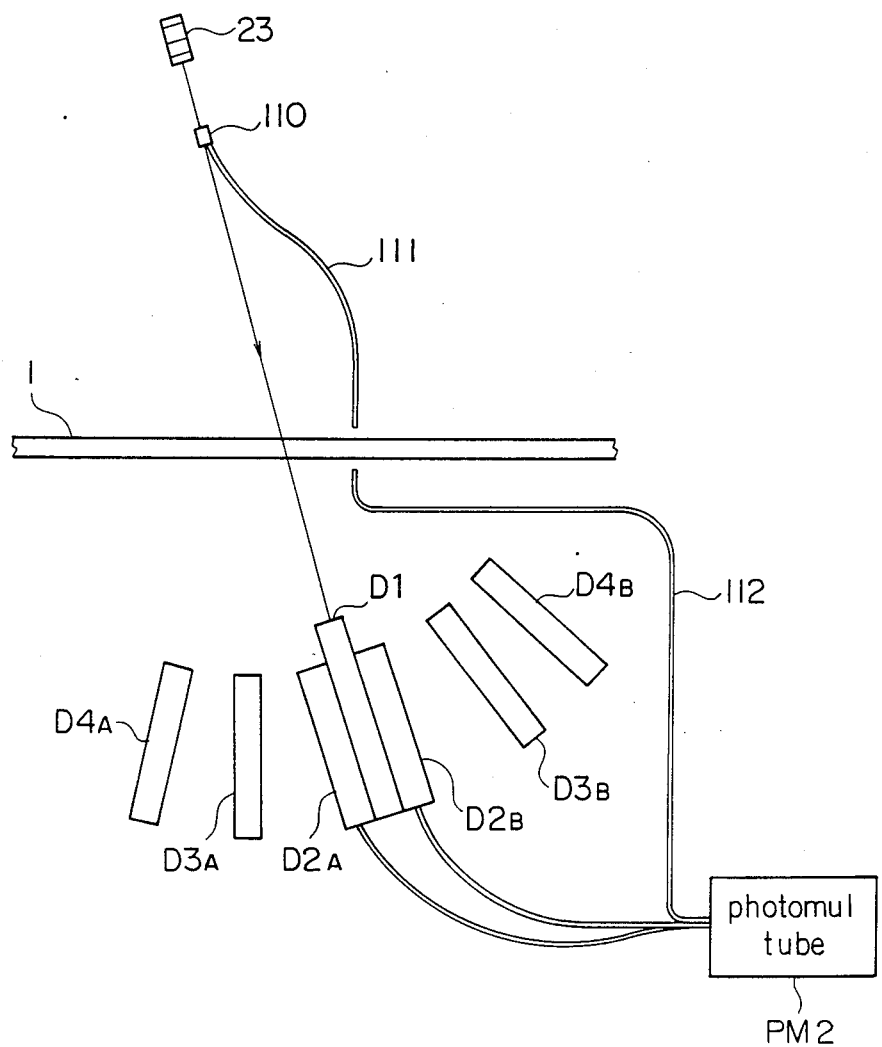

Next, another example of the AGC device will be described. This AGC device relies on a light receptor and an optical fiber, rather than on the light diffuser, for collecting reference light. FIGS. 37A and 37B show such examples where the reference light is collected in the photomultiplier tube PM2, for example; FIG. 37A being a diagram viewed from the Y-axis direction and FIG. 37B being a diagram viewed from the X-axis direction.

In this AGC device, a light receptor 110 is provided above a glass plate 1 and outside the effective scanning range L of a scanning light spot, and one end of an optical fiber 111 is connected to the light receptor, with the other end thereof disposed in the vicinity of the upper surface of the glass plate 1. Another optical fiber 112 is provided below the glass plate 1, with one end thereof disposed in the vicinity of the lower surface of the glass plate 1. In such a manner as to oppose the other end of the optical fiber 111, and the other end thereof connected to the photomultiplier tube PM2 for the most paraxial transmitted and diffused light.

With this AGC device, reference light is collected from the scanning light 26 into the photomultiplier tube PM2 via the optical fibers 111 and 112. An electrical circuit for keeping the level of the reference light at a predetermined level is omitted because it is the same as that in the abovementioned AGC device and has similar functions.

Figure 38:
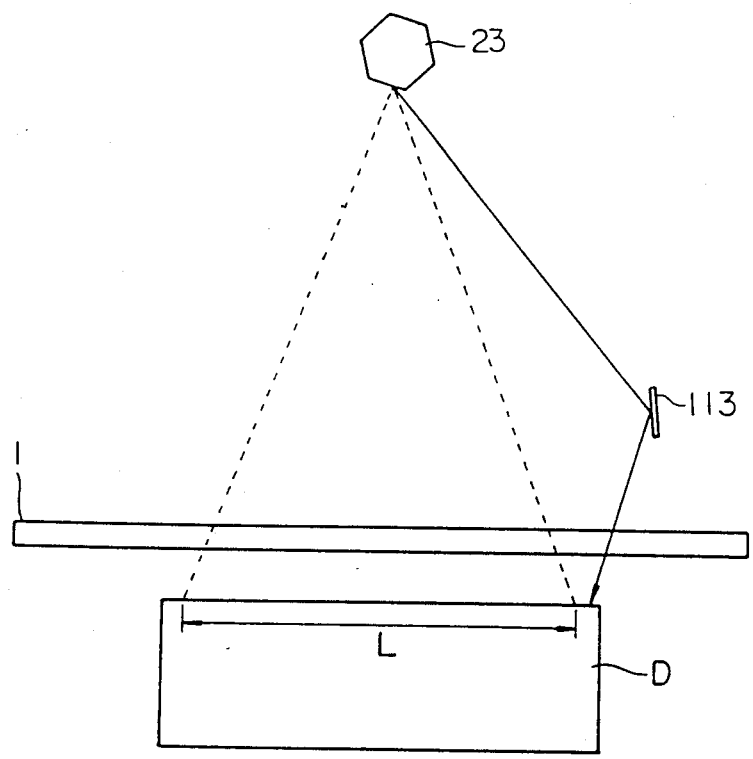
FIG. 38 is a diagram illustrating a third example of the AGC device.

FIG. 38 shows still another example of the AGC device in which a mirror 113 is provided as a means for collecting reference light outside the effective scanning range L of scanning light and above a glass plate 1. The scanning light reflected by the mirror 113 falls on a transmitted and diffused light receptor as reference light, and the automatic gain control of a photomultiplier tube is carried out based on this reference light in the same manner as described in FIG. 35.

Industrial Applicability

The discriminating type flaw detector of this invention makes it possible to detect flaws inside and on the surface of a light-transmitting plate material and discriminate the types and sizes of the flaws with high accuracy and high speed. Thus, generation of flaws can be prevented at the place of generation and product yield can be improved by feeding the detection results back to the glass plate manufacturing process.

By using the discriminating type flaw detector of this invention, flaws, whether large or small, can be detected with high accuracy, and cut-length glass plates can be sorted into high-grade and low-grade ones. This leads to improved glass-plate sorting yield.

By using the discriminating type flaw detector of this invention, moreover, sorting yield can be improved even when sorting cut-length glass plates for automobile windshields, consisting of a high-grade see-through area and a low-grade peripheral area.

In addition, the light receptor, thickness correcting device and AGC device of this invention can be applied not only to the discriminating type flaw detector for light-transmitting plate materials but also to other technical fields.

What is claimed is:

1. A discriminating type flaw detector for light-transmitting plate materials comprising
    light-spot scanning means for scanning a travelling light-transmitting plate material with a light spot;
    light-receiving means having a plurality of light receptors each for receiving each of more than two types of light among transmitted light, transmitted and diffused light, reflected light and reflected and diffused light from said light-transmitting plate material scanned by said light spot;
    photoelectric converting means having a plurality of photoelectric converters each connected to each of said light receptors for converting light received by said corresponding light receptor into an electrical signal;
    flaw data generating means for processing said electrical signal from said photoelectric converting means to generate flaw data containing information on the types and sizes of flaws existing in said light-transmitting plate material;
    flaw data acquisition means for collecting flaw data from said flaw data generating means, combining and processing said collected flaw data to form a flaw pattern indicating the types and sizes of flaws and a flaw location data; and
    information processing means for comparing said flaw pattern with a flaw discriminating pattern table stored in advance to discriminate at least the types and sizes of flaws and discriminate flaw locations based on said flaw location data.

2. A discriminating type flaw detector for light-transmitting plate materials according to claim 1, wherein said light spot scanning means comprises
    a light source for generating a light beam;
    light projecting means for repeatedly projecting a light beam from said light source as scanning light onto said light-transmitting plate material in the direction normal to the travelling direction of said light-transmitting plate material.

3. A discriminating type flaw detector for light-transmitting plate materials according to claim 1 wherein
    at least light receptors each for receiving each of transmitted light and transmitted and diffused light among said light receptors comprise a plurality of optical fibers, one ends of which are arranged in a row to constitute a light-receiving surface, and the other ends of which are connected to said photoelectric converting means.

4. A discriminating type flaw detector for light-transmitting plate materials according to claim 1 wherein said flaw data acquisition means comprises
    a first counter for counting a first pulse train relating to the location of said light-transmitting plate material in the direction normal to the travelling direction thereof and outputting a count value at the time when flaw data is collected;
    a second counter for counting a second pulse train relating to the location of said light-transmitting plate material in the travelling direction thereof and outputting a count value at the time when flaw data is collected;
    an OR unit for accumulating and OR-processing flaw data for a plurality of scans and outputting processed flaw data at the pulse generating timing of said second pulse train; and
    a buffer memory for temporarily storing the outputs of said first counter, second counter and OR unit.

5. A discriminating type flaw detector for light-transmitting plate material according to claim 1 wherein said flaw data acquisition means comprises
    a first counter for counting a first pulse train relating to the location of said light-transmitting plate material in the direction normal to the travelling direction thereof and outputting a count value at the time when flaw data is collected;
    a second counter for counting a second pulse train relating to the location of said light-transmitting plate material in the travelling direction thereof and outputting a count value at the time when flaw data is collected;
    an OR unit for accumulating and OR-processing flaw data for a plurality of scans and outputting processed flaw data at the pulse generating timing of said second pulse train;
    a continuity judgment circuit for compressing flaw data from said OR unit, judging the continuity of said compressed flaw data in said travelling direction and in said direction normal to the travelling direction thereof, and synthesizing a flaw data block; and a buffer memory for temporarily storing the output of said continuity judgment circuit.

6. A discriminating type flaw detector for light-transmitting plate materials according to claim 1 wherein a thickness correcting device for correcting a location at which light falls on said light receptor, when the thickness of said light-transmitting plate material changes, in accordance with said change in thickness;

said thickness correcting device comprising location detecting means for detecting a location at which light falls on said light receptor;

driving means for driving an object being driven to correct said location at which incident light falls on said light receptor; and control means for controlling said driving means in accordance with location information from said location detecting means.

7. A discriminating type flaw detector for light-transmitting plate materials according to claim 1 wherein an AGC device for automatically controlling the gain of said photoelectric converter;

said AGC device comprising reference light collecting means which collects scanning light outside an effective scanning range after said scanning light is caused to transmit through said light-transmitting plate material and fall on a transmitted and diffused light receptor; and control means for controlling the gain of said photoelectric converter connected to said transmitted and diffused light receptor so that the level of said collected reference light is kept at a predetermined level.

8. A discriminating type flaw detector for light-transmitting plate materials according to claim 1 wherein said light-transmitting plate material is a glass plate;

said light receiving means has a first light receptor for receiving transmitted light from said glass plate and a second light receptor for receiving reflected light from said glass plate;

said photoelectric converting means has two photoelectric converters each connected to said first and second light receptors for converting light received by said corresponding light receptors into electrical signals;

said flaw data generating means processes said electrical signals from said photoelectric converting means to produce flaw data containing information on the types and sizes of flaws existing in said glass plate;

said flaw data acquisition means collects flaw data from said flaw data generating means, combines and processes said collected flaw data and forms a flaw pattern indicating the types and sizes of flaws and flaw location data;

said information processing means compares said flaw pattern with a flaw discriminating pattern table stored in advance to identify the type of flaw as a drip and the size of said drip and recognize the location of flaw based on said flaw location data, whereby discriminating and detecting a drip as one of flaws in a glass plate.

9. A discriminating type flaw detector for light-transmitting plate materials according to claim 3 wherein a light diffusion plate is provided in front of the light-receiving surface of a light receptor.

* * * * *